(12) United States Patent
Liu et al.

(10) Patent No.: US 7,968,701 B2
(45) Date of Patent: Jun. 28, 2011

(54) NYLON POLYRIBONUCLEOSIDES

(75) Inventors: Yu Liu, Brooklyn, NY (US); Liang Ding, Ithaca, NY (US); Ruojie Sha, Pomona, NY (US); Nadrian Seeman, New York, NY (US); James Canary, New York, NY (US)

(73) Assignee: New York University, New York, NY (US)

( * ) Notice: Subject to any disclaimer, the term of this patent is extended or adjusted under 35 U.S.C. 154(b) by 337 days.

(21) Appl. No.: 12/193,600

(22) Filed: Aug. 18, 2008

(65) Prior Publication Data
US 2009/0099351 A1 Apr. 16, 2009

Related U.S. Application Data

(60) Provisional application No. 60/956,510, filed on Aug. 17, 2007.

(51) Int. Cl.
C07H 21/00 (2006.01)
(52) U.S. Cl. ............ 536/25.3; 536/22.1; 536/23.1
(58) Field of Classification Search .......... None
See application file for complete search history.

(56) References Cited

U.S. PATENT DOCUMENTS
6,265,558 B1 7/2001 Cook et al.
6,713,602 B1 3/2004 Buchardt et al.
2005/0153926 A1 7/2005 Adams et al.

OTHER PUBLICATIONS

Nielsen, Addressing the challenges of cellular delivery and bioavailability of peptide nucleic acids (PNA), Quarterly Reviews of Biophysics, 38(4)345-350 (2005).
Zhu et al., Nylon/DNA: Single-stranded DNA with a covalently stitched nylon lining, J. Am. Chem. Soc., 125:10178-10179 (2003).
Li et al., DNA-catalyzed polymerization, J. Am. Chem. Soc., 124(5):746-747 (2002).

*Primary Examiner* — Patrick T Lewis
(74) *Attorney, Agent, or Firm* — Browdy and Neimark, PLLC

(57) ABSTRACT

The present invention provides a polyribonucleoside ladder copolymer molecule of general formula (I)

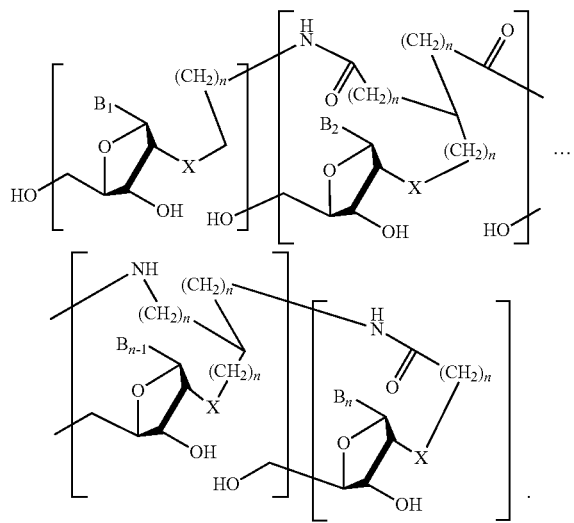

6 Claims, 13 Drawing Sheets

U3a C$_{43}$H$_{62}$N$_8$O$_{17}$S$_3$
Exact Mass: 1058.34

U5 C$_{78}$H$_{108}$N$_{14}$O$_{29}$S$_5$
Exact Mass: 1828.60

U3b C$_{43}$H$_{62}$N$_8$O$_{17}$S$_3$
Exact Mass: 1058.34

U2 : n = 0 C$_{27}$H$_{39}$N$_5$O$_{11}$S$_2$
Exact Mass: 673.21

U4 : n = 1 C$_{59}$H$_{85}$N$_{11}$O$_{23}$S$_4$
Exact Mass: 1443.47

U6 : n = 2 C$_{91}$H$_{131}$N$_{17}$O$_{35}$S$_6$
Exact Mass: 2213.73

U8 : n = 3 C$_{123}$H$_{177}$N$_{23}$O$_{47}$S$_8$
Exact Mass: 2986.4

SEQUENCE LISTING

<160> NUMBER OF SEQ ID NOS: 5

<210> SEQ ID NO 1
<211> LENGTH: 46
<212> TYPE: DNA
<213> ORGANISM: Artificial
<220> FEATURE:
<223> OTHER INFORMATION: synthetic

<400> SEQUENCE: 1
gtagaaaaaa aaatatgccg tgcatacgac ttttgtcgta tgcacg          46

<210> SEQ ID NO 2
<211> LENGTH: 46
<212> TYPE: DNA
<213> ORGANISM: Artificial
<220> FEATURE:
<223> OTHER INFORMATION: synthetic

<400> SEQUENCE: 2
gcacgtatgc tgttttcagc atacgtgccg tatcaaaaaa cagatg          46

<210> SEQ ID NO 3
<211> LENGTH: 46
<212> TYPE: DNA
<213> ORGANISM: Artificial
<220> FEATURE:
<223> OTHER INFORMATION: synthetic

<400> SEQUENCE: 3
gcacgtatgc tgttttcagc atacgtgccg tataaaaaaa aagatg          46

<210> SEQ ID NO 4
<211> LENGTH: 18
<212> TYPE: DNA
<213> ORGANISM: Artificial
<220> FEATURE:
<223> OTHER INFORMATION: synthetic

<400> SEQUENCE: 4
gcatagtttt ttgtctac          18

<210> SEQ ID NO 5
<211> LENGTH: 18
<212> TYPE: DNA
<213> ORGANISM: Artificial
<220> FEATURE:
<223> OTHER INFORMATION: synthetic

<400> SEQUENCE: 5 gcatatttttttttctac          18

NYLON POLYRIBONUCLEOSIDES

CROSS-REFERENCE TO RELATED APPLICATIONS

The present application claims priority from U.S. provisional application No. 60/956,510, filed Aug. 17, 2007, the entire content of which is hereby incorporated by reference.

GOVERNMENT LICENSE RIGHTS

The experiments performed in this application were supported in part by the National Science Foundation, grants CTS-0548774, CTS-0608889, CHE-0316589, by the National Institute of General Medical Sciences, grants DMI-0210844, EIA-0086015, CCF-0432009, CCF-0523290, GM-076202 and GM-29554, by ARO (48681-EL), and by a subcontract from the Research Foundation of SUNY, prime contractor of grant DE-FG02-06ER64281 from the Department of Energy. The U.S. Government has a paid-up license in this invention and the right in limited circumstances to require the patent owner to license others on reasonable terms as provided for by the terms of the above grants.

BACKGROUND OF THE INVENTION

1. Field of the Invention

The present invention relates to nylon nucleic acids and nylon polymers that contain pendant nucleosides.

2. Description of the Related Art

In addition to its essential role in life involving the storage and expression of genetic information, the applications of DNA have expanded beyond biology. Owing to its outstanding molecular recognition and self-assembly properties and relatively simple and stable structure, DNA molecules have also been utilized as linkers or templates to assemble many nanostructures (Seeman, 2003) and hetero-species, (Katz et al., 2004) such as fullerenes (An et al., 1996; and Bergamin et al., 2001), nanoparticles (Zheng et al., 2006; and Merkoci et al., 2005; Sato et al., 2007) or carbon nanotubes (Li et al., 2005; Wooley, 2005; Katz et al., 2004; and Zuccheri et al., 2005) and to construct hybrid nanostructures or nanodevices, such as nanowires (Braun et al., 1998; Richter et al., 2001; Woolley, 2003 and Burley et al., 2006), field-effect transistors (Keren et al., 2003), luminescent sensors or electronic sensors (Li et al., 2003; He et al., 2004; Staii et al., 2005; and Briones et al., 2006) and nanomechanical devices (Fritz et al., 2000; Seeman, 2005; and Bath et al., 2007). However, far fewer stereo- and regio-specific DNA-mediated polymer syntheses are known (Datta et al., 2006 and 2008; Kleiner et al. 2008).

Recently, the laboratories of the present inventors have reported the use of DNA as a scaffold for the construction of a nylon-like polymer (Zhu et al., 2002 and 2003). In that study, the 2' position of an RNA analog nucleoside was derivatized with diamino or dicarboxyl groups; the pendent groups were condensed into a short nylon-like molecule (see the nylon nucleic acid synthesis in FIG. 1). The long-term goal of this work is to use the topological control afforded by nucleic acids (Rothemund et al., 2006; Lund et al., 2006; Seeman, 2005; and Feldkamp et al., 2006) to direct the topology of polymers with industrial importance. In the design of the strands reported in the earlier work from the laboratories of the present inventors, a 16-mer with four nylon nucleic acid residues flanked by polythymidine, 5'-(dT)$_6$ UcUnnUccUn(dT)$_6$, was synthesized via single-stranded amide ligation from an uncoupled precursor strand. The notation, which will be used in the specification throughout, indicates uridine nucleotides containing single amino or carboxyl modifications as Un or Uc, respectively, and diamino or dicarboxyl modifications are labeled as Unn or Ucc, respectively (FIG. 2). The coupled products (i.e., nylon nucleic acids) are indicated by an underline at the coupled nucleotides (e.g., UnUc). Thus, the previous nylon nucleic acid was synthesized with only thymidine and modified uridine residues. The disadvantage of an oligonucleotide whose nucleotides consist entirely of rU or dT is that there is no control over the position or manner in which it binds its oligo-dA complement; the possibility of triple helix formation is another confounding factor (Felsenfeld, 1957). To realize nylon polymer synthesis programmed by base pairing, heterobase oligonucleotides or polynucleotides must be utilized.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

The present invention provides a polyribonucleoside ladder copolymer molecule having a structure that includes the general formula (I), which is preferably a nylon polyribonucleoside molecule with a nylon backbone having a structure that includes general formula (III)

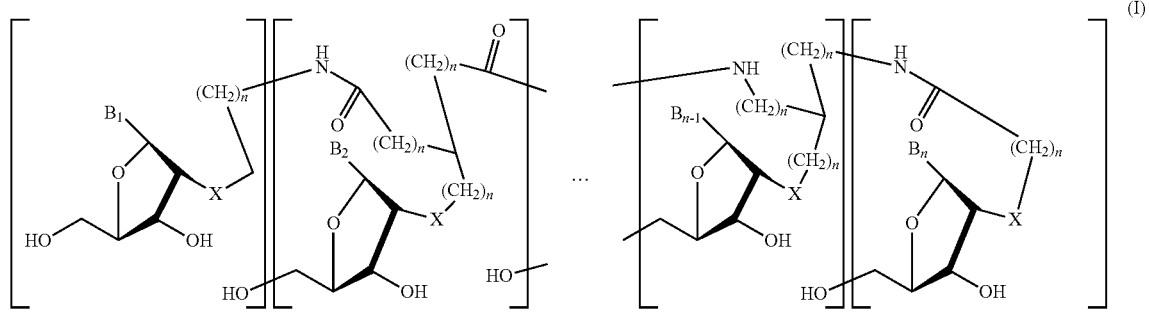

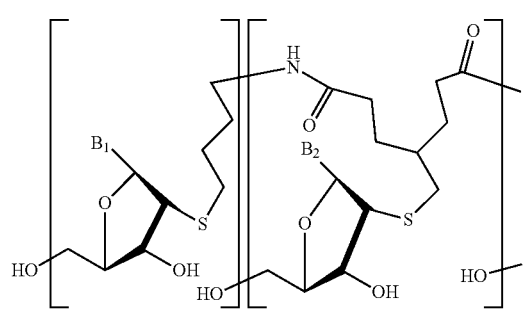
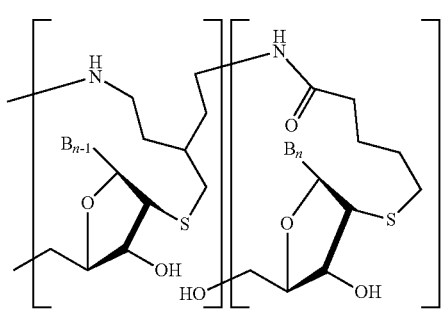

(III)

where $B_1$ to $B_n$ is independently a base selected from the group consisting of uracil, thymine, adenine, guanine, cytosine, and modified pyrimidines and purine bases and X=O, S or NH.

The present invention also provides a method for preparing the ladder copolymer polyribonucleoside molecule from a nucleic acid molecule of formula (II), which is preferably a nylon polyribonucleside molecule of formula (IV).

then connected using chemical ligation. The nylon nucleic acid product 9b is separated from hairpin template by denaturing gel electrophoresis.

FIG. 3 is a non-denaturing gel electrophoresis of nylon nucleic acid to check both annealing with a complementary hairpin DNA and coupling. Lane 1: 10 Nucleotide pair marker ladder, Lane 2: Uncoupled precursor strand 5a, Lane 3: Hairpin 5a (before adding coupling agent, hairpin DNA is in 1.1 equivalence), Lane 4: Hairpin: 5b after coupling (Note minimal effects on mobility, because the net charge is not altered) and Lane 5: Hairpin.

FIG. 4A is a comparison of MALDI-TOF MS of (A) the precursor strand 6a, (B) DNA templated synthesis of nylon nucleic acid 6b, and (C) single-stranded synthesis of nylon nucleic acid 6b and FIG. 4B is a comparison of MALDI-TOF MS of (A) the precursor strand 7a, (B) DNA templated synthesis of nylon nucleic acid 7b, and (C) single-stranded synthesis of nylon nucleic acid 7b.

FIG. 5A is a comparison of MALDI-TOF mass spectra of (A) the uncoupled precursor strand 8a, (B) DNA templated

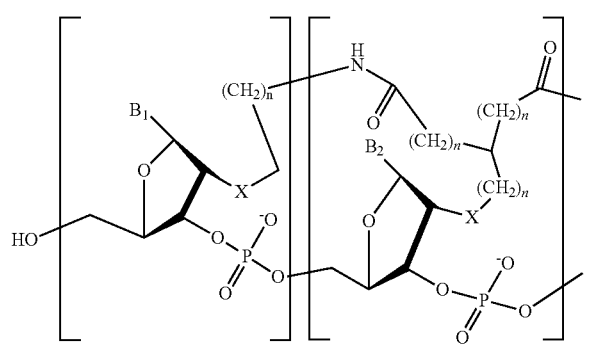
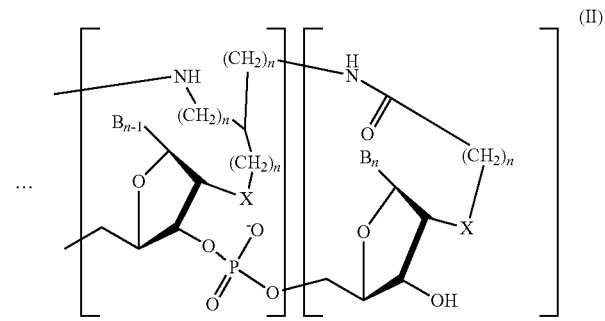

(II)

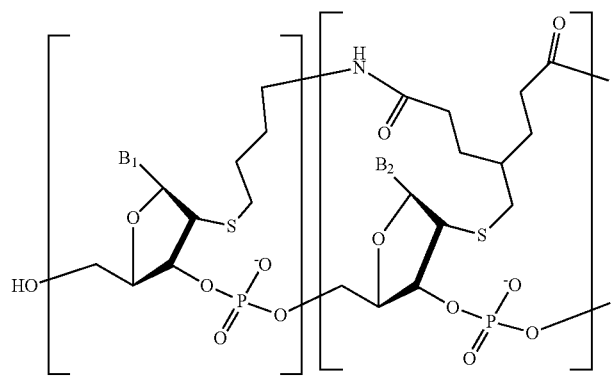
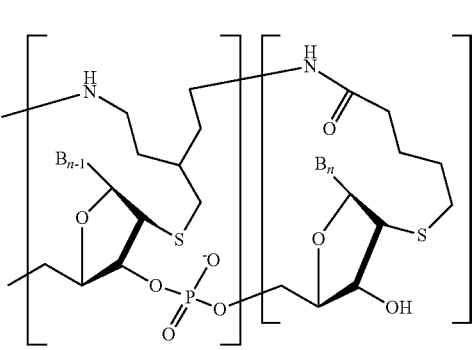

(IV)

BRIEF DESCRIPTION OF THE DRAWINGS

(FIG. 9A) UV chromatogram of DNA 1 digest, (FIG. 9B) UV chromatogram of nylon nucleic acid 3b digest, (FIG. 9C) UV chromatogram of nylon nucleic acid 4b digest, (FIG. 9D) UV chromatogram of nylon nucleic acid 5b digest, (FIG. 9E) UV chromatogram of nylon nucleic acid 6b digest and (FIG. 9F) UV chromatogram of nylon nucleic acid 7b digest. Items (FIG. 9G) ESI mass spectrum and (FIG. 9H) MALDI-TOF mass spectrum of U5 are shown as examples. The LC eluates were analyzed directly by ESI-MS. The oligouridines were isolated from the digestion reaction by HPLC before MALDI-TOF MS analysis.

(FIG. 10A) UV chromatogram of DNA 1 digest, (FIG. 10B) UV chromatogram of nylon nucleic acid 8b digest, (FIG. 10C) UV chromatogram of DNA 2 digest, (FIG. 10D) UV chromatogram of nylon nucleic acid 9b digest, (FIG. 10E) ESI mass spectrum of U6 eluate from the LC separation with target mass of quadruple ion trap control set to [M], both mono-ionic peaks ([M+1]$^+$, [M+Na]$^+$) and bi-ionic peaks ([M+2H]$^{2+}$, [M+2Na]$^{2+}$) are shown, (FIG. 10F) MALDI-TOF mass spectrum of U6, (FIG. 10G) ESI mass spectrum of U8 with target mass of quadruple ion trap control set to [M], only mono-ionic peak ([M+Na]$^+$) is shown, (FIG. 10H) ESI mass spectrum of U8 with target mass of quadruple ion trap control set to [M/2], both bi-ionic peaks ([M+2H]$^{2+}$, [M+2Na]$^{2+}$) and tri-ionic peak ([M+3H]$^{3+}$) are shown, (FIG. 10I) MALDI-TOF mass spectrum of U8, peak corresponding to losing a uracil base fragment is marked with an asterisk (*). The LC eluates were analyzed directly by ESI-MS. The oligouridines were isolated from the digestion reaction by HPLC before MALDI-TOF MS analysis.

(FIG. 11A) UV chromatogram, (FIG. 11B) extracted ion chromatography with target mass 112.4 (deoxycytosine), (FIG. 11C) extracted ion chromatography with target mass 156.1 (deoxyguanine), (FIG. 11D) extracted ion chromatography with target mass 152.1 (deoxyadenine), (FIG. 11E) extracted ion chromatography with target mass 127.5 (deoxythymine), (FIG. 11F) extracted ion chromatography with target mass 332.1 (Un nucleoside), (FIG. 11G) extracted ion chromatography with target mass 375.2 (Uc nucleoside), (FIG. 11H) extracted ion chromatography with target mass 383.3 (Unn nucleoside) and (FIG. 11I) extracted ion chromatography with target mass 433.1 (Ucc nucleoside).

(FIG. 12A) U2 from digestion of 3b, (FIG. 12B) U3a from digestion of 4b, (FIG. 12C) U3b from digestion of 5b and (FIG. 12D) U4 from digestion of 6b. All mass spectra show [M+H]$^+$ peak and [M+Na]$^+$ peak.

DETAILED DESCRIPTION OF THE INVENTION

Figure 1:
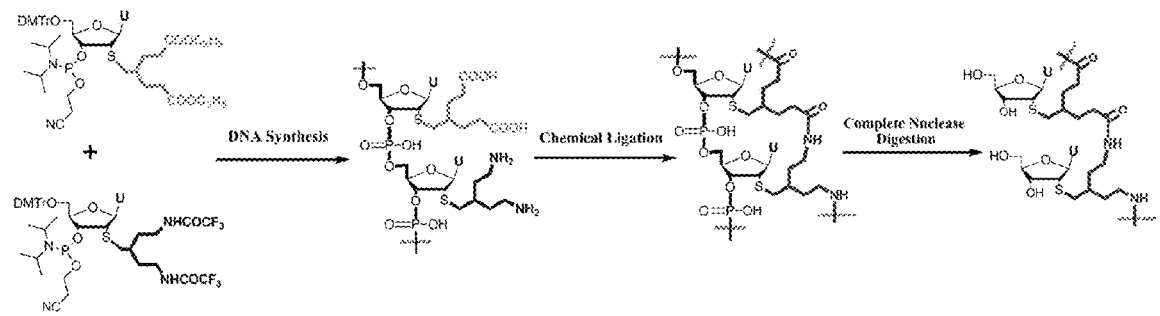
FIG. 1 is a schematic illustration of nylon nucleic acid synthesis and complete nuclease digestion. Dicarboxyl pendent group and diamino pendent groups, the phosphate backbone, and the nylon backbone are shown. U: uracil.

Nylon nucleic acid has a nucleic acid-based ladder polymer, in which DNA is covalently linked to a nylon polymer through the 2' position of each nucleotide. The present inventors have synthesized nylon nucleic acid, using a complementary hairpin strand as a template (FIG. 2). The synthesis efficiency of the templated approach was compared with single stranded synthesis by Maldi-TOF MS. The templated synthesis approach gave a much higher coupling yield; incompletely coupled or other byproducts were not detected. To determine the possibility of topological isomer formation during templated synthesis, nylon nucleic acid molecules were subjected to full digestion with exonucleases, i.e., snake venom phosphodiesterase (SVP) and bacterial alkaline phosphatase (BAP), followed by LCMS analysis. The products of digestion are unique 2' peptide linked oligonucleosides. Analysis of LCMS traces and integration provided further evidence that the templated synthesis strategy affords the correct topological isomer and is heteronucleotide-compatible.

The polyribonucleoside molecule of the present invention has the general formula (I)

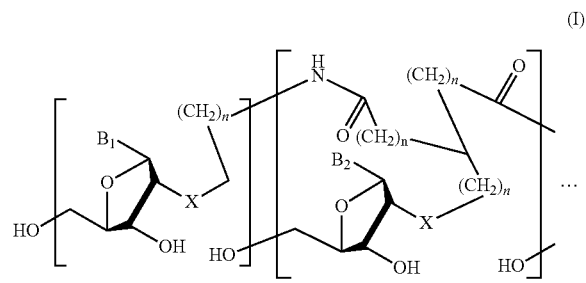

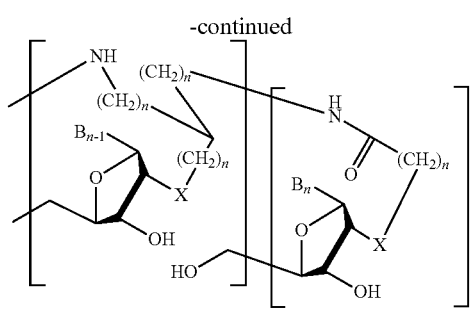

where $B_1$ to $B_n$ is independently a base selected from uracil, thymine, adenine, guanine, cytosine, and modified pyrimidine and purine bases and where X=O, S or NH. A preferred embodiment of the polynucleoside molecule is the nylon polyribonucleoside molecule having formula (III)

(III)

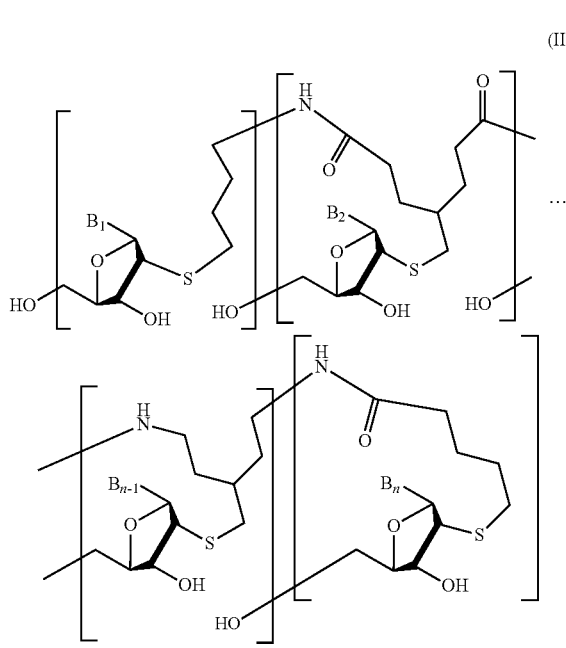

The polyribonucleoside molecule having formula (I) or (III) according to the present invention can have varying length, i.e., where n as it relates to the base B in formula (I) or (III) is in a range of 5 to 50, 8 to 50 or 10 to 50, more preferably 5 to 40, 8 to 40 or 10 to 40, most preferably 5 to 30, 8 to 30 or 10 to 30.

The bases (B) may be bases other than the standard five, adenine (A), cytosine (C), guanine (G), thymine (T), and uracil (U), including modified pyrimidine and purine bases which are intended to be bases that are chemically modified (e.g., methylated) as well as other unusual bases such as iso-guanine, iso-cytosine, amino-adenine, K, X, pi, inosine. Some examples of modified pyrimidine and purine bases are presented in Freier et al. (1997), which is incorporated herein by reference. A preferable feature in the selection of the bases is that they be capable of interacting with a base opposing them to form a specifically paired attraction. In natural DNA and RNA, hydrogen bonding forms this interaction. However, opposite ion charges, hydrophobic interactions and van der Waals forces may also be acceptable forms of interaction. These interactions expand the choices over naturally occurring bases to give a wider assortment of physical properties.

The nylon/polyamide backbone shown in formula (III) approximates the equivalent of Nylon-5,7. Other suitable polyamide or nylon backbones can be used in the ladder copolymer of the present invention. See for example, Kirk-Othmer *Encyclopedia of Chemical Technology*, 4$^{th}$ ed., editors J. I. Kroschwitz and M. Howe-Grant, John Wiley & Sons, New York, volume 19, pages 454-559 on polyamides (general) and polyamides in fibers, the entire contents of which are incorporated herein by reference.

The present invention is also directed to a method for preparing the polyribonucleoside molecule of the present invention by enzymatically digesting a nucleic acid molecule of formula (II)

(II)

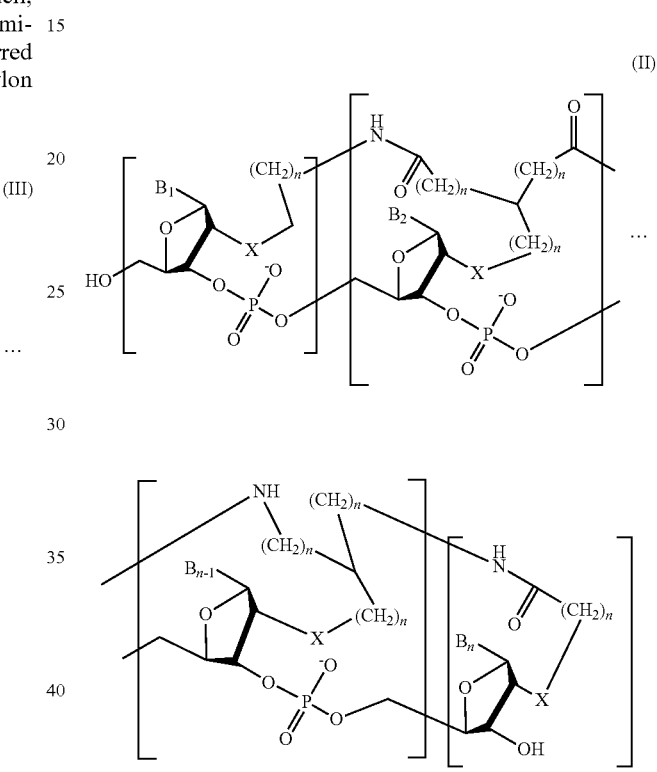

with a phosphodiesterase enzyme, i.e., preferably snake venom phosphodiesterase (SVP), and a phosphatase enzyme, i.e., preferably bacterial alkaline phosphatase (BAP). A preferred embodiment of the nucleic acid molecule of formula (II) used in the present method is a nylon nucleic acid molecule of formula (IV)

(IV)

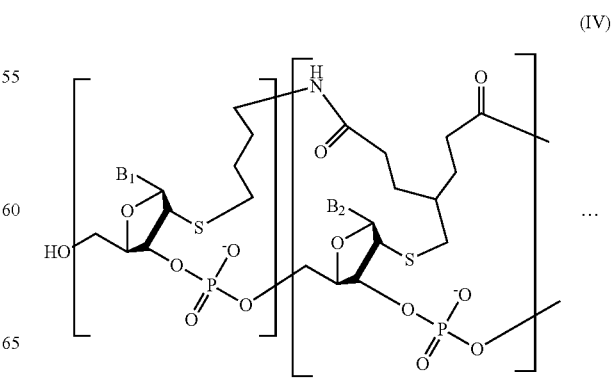

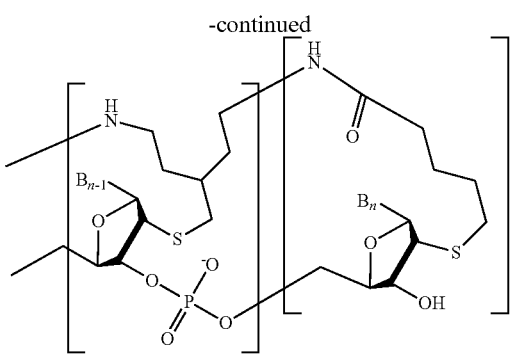

The synthesis of the nylon nucleic acid molecule of formula (IV) is described in WO2005/001035, which is incorporated herein by reference, and involves synthesizing 2'-β-substituted phosphoramidites, then synthesizing oligonucleotides with pendent groups from the synthesized 2'-β-substituted phosphoramidites, followed by coupling the pendent groups to produce a ladder copolymer.

It should also be appreciated by those of skill in the art that the nylon polyribonucleoside molecule of the present invention can also be produced by peptide synthesis techniques well known in the art.

The nylon polyribonucleoside molecule of the present invention, which is a nylon polymer with pendant ribonucleosides, is similar in structure to peptide-nucleic acid (PNAs) and peptide ribonucleic acids (PRNAs) (Nielsen, 2003; Harris et al., 2005; Sato et al., 2004; and Wada et al., 2000). It is a neutral molecule that present nucleobases in a geometry complementary to DNA or RNA, and like PNAS, has utility in material science applications and in biomedical applications such as aptamers, antisense and related therapeutic strategies, i.e., siRNA in RNAi;

The nylon polyribonucleoside molecule of the present invention is expected to be superior to PNA due to the presence of the ribose units which PNA lacks. Thus, the nylon polyribonucleoside molecule has all the properties of a nucleic acid, while lacking nuclease susceptibility. This molecule also offers some additional capabilities that PNA and similar compounds lack. For example, the hydroxyl groups available on the ribose moieties may be used to "trigger" on/off antisense properties by using boranes or similar groups that can be added or removed conveniently (see Wada et al., 2000, which is based on a peptide backbone with links to the 5'-position of the nucleosides). The nylon polyribonucleoside molecule of the present invention would still be expected to be superior because it is generated from nylon nucleic acid, which has been shown to form complementary complexes with DNA and RNA.

Having now generally described the invention, the same will be more readily understood through reference to the following example which is provided by way of illustration and is not intended to be limiting of the present invention.

EXAMPLE

Figure 2A:
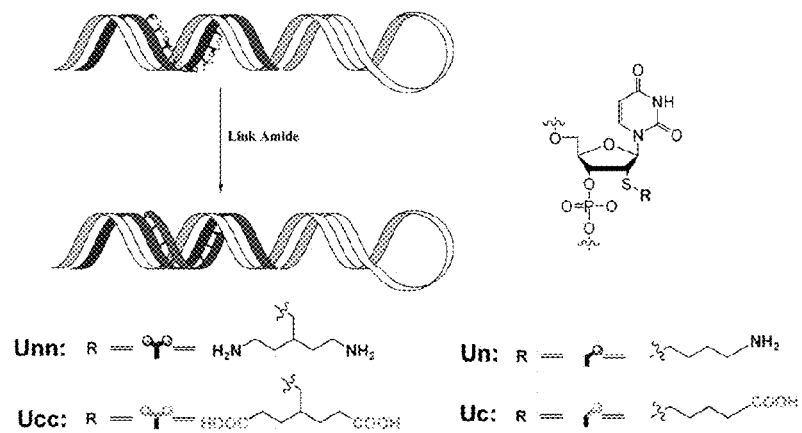
FIGS. 2A and 2B are schematic depictions of templated synthesis of nylon nucleic acid 9b in the Example hereinbelow. A DNA hairpin template strand 9a (SEQ ID NO:1) with a complementary sequence to the nylon nucleic acid strand forms a stable duplex. Proximal amines and carboxylates are synthesis of nylon nucleic acid 8b (coupling reagent, DMTMM, was added only once), (C) DNA templated synthesis of nylon nucleic acid 8b (coupling reagent, DMTMM, was added twice at an interval of 24 h) and (D) single-stranded synthesis of nylon nucleic acid 8b (without template)
Figure 2B:
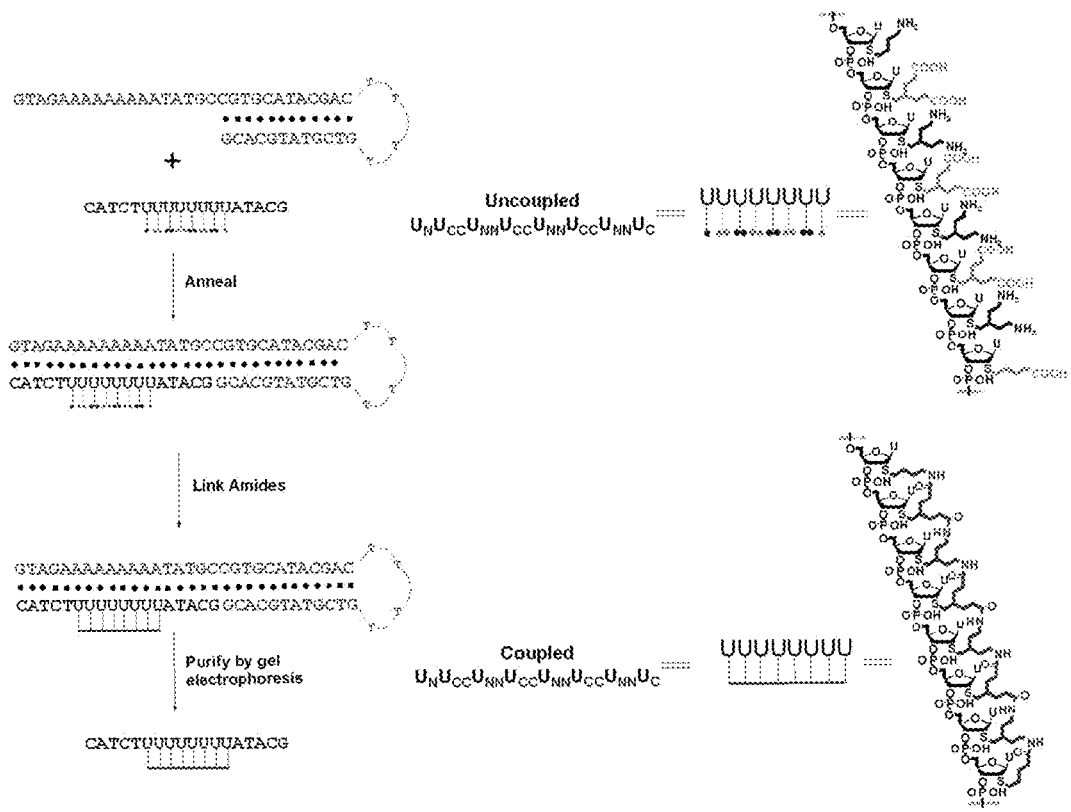

A series of nylon nucleic acids containing oligouridine nucleotides with pendent alkyl amines and carboxylates and flanked by normal heteronucleotide sequences was synthesized using a complementary DNA hairpin molecule as a template (FIGS. 2A and 2B). As evaluated by MALDI-TOF MS, the templated synthesis gave much higher coupling efficiency than single stranded synthesis. Coupling step yields as high as 99.2% were obtained, with up to 7 amides formed in the synthesis of a nylon nucleic acid molecule containing 8 nucleotides with pendent groups. To clarify the topology of the oligo-amide linkages in nylon nucleic acid, a simple and practical method was developed. The method involves nuclease degradation of nylon nucleic acid and dephosphorylation of nucleotides, followed by LCMS analysis. The unique digestion products, oligomers of nucleosides linked together by 2'-thioalkyl tethers, were detected by ESI-MS.

Controlled exonuclease digestion followed by MALDI-TOF MS analysis of the mass ladders has been used to determine DNA sequence (Limbach, 1996; and Smirnov et al., 1996), to locate DNA lesions (Tretyakova et al., 2001), to identify DNA secondary structure (Bartolini et al., 1999), and to study the binding of small molecules to DNA (Asara et al., 2000). As another efficient tool for DNA analysis, complete exonuclease digestion combined with LCMS analysis (Banoub et al., 2006) has been applied to the detection of DNA adducts (Andrews et al., 1999; Koc et al., 2002; Singh et al., 2006), DNA nucleobase lesions (Roberts et al., 2006; Budzinski, 2002), post-transcriptional modification of RNAs Kowalak et al., 2000; McCloskey et al., 2001), and DNA-metal complex interactions (Barry et al., 2003). In this study, both exonuclease digestion methods were employed to allow not only the location and identification of the modified regions of nylon nucleic acid (FIG. 1), but also to provide quantification of base composition. Controlled digestion by calf spleen phosphodiesterase (a 5'-3' exonuclease) enabled the mapping of modified nucleotides in the sequences. A combination of complete degradation of nylon nucleic acids by snake venom phosphodiesterase (a 3'-5' exonuclease) and dephosphorylation of mononucleotides by bacterial alkaline phosphatase followed by LCMS analysis clarified the linear structure of the oligo-amide linkages and provided quantitative evidence that the templated synthesis strategy affords nylon nucleic acid in the desired structure and that it is heteronucleotide-compatible. The complete digestion products are unique nylon oligomers with nucleosides attached to each diamine and dicarboxylate repeating unit. The expected 2'-peptide-linked oligonucleosides from complete exonuclease digestion of nylon nucleic acids were isolated and tested for binding affinity to complementary DNA by thermal denaturing experiments.

Materials and Methods

Materials. All buffer solutions were prepared from analytically pure chemicals and doubly distilled water and adjusted to desired pH values. Phosphodiesterase II, calf spleen phosphodiesterase (CSP, 5'-3' exonuclease) was purchased from Sigma-Aldrich (St. Louis, Mo.), bacterial alkaline phosphatase (BAP) and 10×BAP buffer were purchased from Invitrogen (Carlsbad, Calif.) and phosphodiesterase I, snake venom phosphodiesterase (SVP, 3'-5' exonuclease) was purchased from USB Corp (Cleveland, Ohio). The preparation of the modified phosphoramidite uridine monomers and synthesis of nylon nucleic acid precursor strands followed the procedures previously reported, (Zhu et al., 2002, 2003) except that strands were cleaved from resin and deprotected at 50° C., instead of room temperature. Compound $dU_8$ was synthesized by automatic DNA synthesizer with deoxyuridine support and phosphoramidite purchased from Glen Research (Sterling, Va.). The complementary hairpin DNA 46mer for templated nylon nucleic acid synthesis and the normal DNA 1, 2 and $dA_8$ were obtained from Integrated DNA Technologies (Coralville, Iowa). All the commercial DNA strands and synthesized nylon nucleic acid precursor strands were purified either by denaturing gel electrophoresis (20% acrylamide; running buffer contains 89 mM Tris.HCl, pH 8.0, 89 mM Boric acid, and 2 mM EDTA) or by HPLC (eluents: 20 mM phosphate buffer, pH 7.0/methanol). The complementary hairpin DNA and nylon nucleic acid precursor strands were further desalted by HPLC (eluents: water/acetonitrile). Strands desalted by HPLC is indispensable to high-yield templated coupling without side reactions. Concentrations of oligonucleotides were determined by UV spectroscopy ($OD_{260}$).

Hairpin 1:
(SEQ ID NO: 2)
5'-GCACGTATGCTGTTTTCAGCATACGTGCCGTATCAAAAAACAGATG was used as template for nylon nucleic acids 3b-8b synthesis.

Hairpin 2:
(SEQ ID NO: 3)
5'-GCACGTATGCTGTTTTCAGCATACGTGCCGTATAAAAAAAAGATG was used as template for nylon nucleic acid 9b synthesis.

DNA templated nylon nucleic acid synthesis. The nylon nucleic acid precursor strand (15 nmol) and 16.5 nmol (1.1 equivalent) complementary hairpin DNA strand were dissolved in 700 µL MOPS buffer (0.1M MOPS, 1.0M NaCl, pH 7.0) in an Eppendorf vial. The resulting solution was annealed overnight from 90° C. to room temperature. A 2 µL aliquot was subjected to non-denaturing gel electrophoresis to check the formation of duplex. The condensing agent DMTMM (13.8 mg, 0.05 mmol) was dissolved in 200 µL MOPS buffer, 150 µL DMTMM solution (250 mM) was added into nylon nucleic acid precursor strand hairpin DNA duplex solution. The reaction solution was mixed with the pipette and centrifuged before incubating at room temperature for 48 hr. For nylon nucleic acid 8b and 9b, an additional 120 µL DMTMM solution (250 mM) was added after 24 hr of reaction. After coupling, another 2 µL aliquot was checked by non-denaturing gel electrophoresis to confirm that the oligonucleotides were still in duplex form. The reaction solution was subjected to ethanol precipitation or filtration through a G25 cartridge in order to remove most of the salt before mass analysis and purification by denaturing gel electrophoresis.

Maldi-TOF MS analysis. Maldi-TOF mass spectra were recorded on a Bruker OmniFLEX Maldi-TOF spectrometer. Procedure for characterization of nylon nucleic acids and precursor strands: A 3-HPA matrix solution was prepared by dissolving 3-HPA (18 mg) in $CH_3CN$ (150 µL) and $H_2O$ (150 µL). An ammonium citrate co-matrix solution was prepared by dissolving ammonium citrate (35 mg) in $H_2O$ (1 mL). The working matrix solution was obtained by mixing 40 µL 3-HPA matrix solution and 10 µL ammonium citrate co-matrix solution. An oligonucleotide sample (20~100 µM, 2 µL) was mixed with the working matrix solution (2.5 µL) using a vortex and then centrifuged. The mixture solution was incubated in $NH_4^+$ exchanged cation resin for 3 min, and 0.9 µL supernatant was deposited in each well on a target. ODNs with known masses were used as either external or internal calibrations in the measurements. Maldi-TOF mass spectra were recorded in positive mode. Procedure for characterization of nylon linked oligouridines, the complete nuclease digestion products: A α-cyano-4-hydroxycinnamic acid (CHCA) matrix solution was prepared by dissolving CHCA (20 mg) in $CH_3CN$ (500 µL) and $H_2O$ (500 µL) containing 0.1% TFA. The neutral uridine oligoribonucleoside sample (2~10 µM, 2 µL) was mixed with the CHCA solution (2 µL) using a vortex mixer and then centrifuged. The mixture was deposited on a target. Peptides or proteins with known masses were used as calibrants in each measurement.

Phosphodiesterase II controlled digestion for ODNs sequencing. The controlled digestion procedure followed slight modification of the reported protocol (Chou et al., 2000). ODN (500 pmol in 5 µL water) was mixed with phosphodiesterase II (calf spleen phosphodiesterase, CSP) solution (5 milliunits in 5 µL water) and ammonium citrate water solution (1 µL, 50 g/L). After vortex mixing and centrifuge, the mixture was incubated at 37° C. Aliquots (1 µL) were removed after 0.5, 2, 4, 9, 15, 20, 30, 40, 60, 240 min and quickly mixed with trihydroxyacetophenone (THAP, as MALDI-TOF matrix) solution (1 µL, 30 mg in 1 mL methanol) before being placed in dry ice to quench the reaction. All digestion aliquots were spotted on a target and analyzed by MALDI-TOF MS.

Phosphodiesterase I/bacterial alkaline phosphatase complete enzymatic digestion. DNA or nylon nucleic acid (200 pmol) was dissolved in 15 µL 1×BAP buffer (diluted from 10×BAP buffer) containing 16 mM $MgCl_2$, 1 unit bacterial alkaline phosphatase (BAP) and 0.5 units Phosphodiesterase I (SVP). The digestion solution was incubated at 37° C. for 12 hr and then at room temperature for 24 hr. Thereafter, an additional 0.8 units bacterial alkaline phosphatase and 0.4 units Phosphodiesterase I was added into the digestion solution which was incubated at 37° C. for another 12 hr. For nylon nucleic acid 6b and 8b, further 48 hr incubation at room temperature in the end is necessary to afford exhaustive digested products. The final mixture solution was directly subject to LCMS analysis without further purification.

LCMS analysis of complete nuclease digests of ODNs. The analysis of digested products by LCMS was conducted on an Agilent 1100 serial Capillary LCMSD Trap XCT system equipped with atmospheric pressure electrospray ionization source. Either a 2.1 mm×150 mm Zorbax SB-C18 column (particle size, 5 µm, Agilent Technologies) or a 2.1 mm×50 mm Zorbax SB-C8 column (particle size, 5 µm, Agilent Technologies) was used for the separation of the nuclease digestion products. A 6 µL portion of digestion solution was injected onto the analytical column thermostated at 30° C. Eluent: A, water containing 0.1% formic acid; B, methanol containing 0.1% formic acid. Gradient for nylon nucleic acid and normal DNA digest is: 0 min, 95% A; 2 min, 95% A; 5 min, 65% A; 40 min, 15% A; 45 min, 0% A. Gradient for precursor strands digest is: 0 min, 100% A; 5 min 100% A; 35 min, 95% A; 70 min, 15% A. The flow rate was 200 µL/min. The effluent was monitored by UV absorption detection at 254 nm. Electrospray source conditions were 8 L/min drying gas flow rate, 40.0 psi nebulizer pressure and 350° C. drying temperature. Mass spectra were recorded in positive mode and target mass of ion trap was set to the mass of uridine oligomer from individual digestion experiments. For analysis of nylon nucleic acids 3b, 7b digests scan range was 50-2200 m/z (Ultra Scan Mode) and for analysis of nylon nucleic acid 8b, 9b digests scan range was 200-4000 m/z (Extended Mode). Only Ultra Scan Mode can afford isotopic mass peaks. All data were analyzed using the LC/MSD Trap Control 4.0 data analysis software.

HPLC separation of complete nuclease digests of nylon nucleic acids. Complete nuclease digestion products were chromatographed on a Zorbax C8 analytical column (4.6 mm×50 mm, 5 µm Agilent Technologies). Eluents: A, water; B, acetonitrile. Gradient: 0 min, 100% A; 2 min 100% A; 3 min, 93% A; 25 min, 73% A. Flow rate: 1 mL/min. The effluent was monitored by UV absorption detection at 260 nm. After removal of solvent by vacuum spinner, the fraction containing oligouridine nucleosides was re-dissolved in water and subject to MALDI-TOF MS analysis.

Thermal denaturing studies. Pairs of complementary strands (45 nmol each) were dissolved in a buffer with stated salt concentrations to a final volume of 120 µL. The solution was annealed overnight from 70° C. to room temperature. The samples were transferred to quartz cuvettes with 1 mm path length, 100 µL volume and the buffer was used as a blank. Thermal denaturation was monitored at 260 nm on a Cary 100 Bio spectrometer. At least two consecutive heating-cooling cycles were applied with a linear temperature gradient of 0.1° C./min. Absorbance vs. temperature curves were converted into θ vs. temperature curves (where θ is the fraction of oligomers in the associated state) by subtracting upper and lower base lines. These upper and lower linear base lines define temperature-dependent extinction coefficients for associated and dissociated states. $T_m$ is defined as the temperature at which half of the strands are in the associated form and half in the dissociated form, i.e. θ=0.5. (Mergny et al., 2003) Only $T_m$ of U8: $dA_8$ duplex in water, 10 mM phosphate buffer, 100 mM NaCl/10 mM phosphate buffer can be determined. No $T_m$ can be extracted from other melting curves due to the lack of UV transition or lack of lower base lines.

Results and Discussion

DNA templated synthesis of nylon nucleic acid. In a previous nylon nucleic acid report from the laboratories of the present inventors, a 16-mer with four nylon nucleic acid residues flanked by polythymidine 5'-$(dT)_6U_CU_{NN}U_{CC}U_N(dT)_6$ was synthesized via single-stranded amide ligation from an uncoupled precursor strand. Our notation is to indicate a pendent alkylamine by a subscripted 'N', a pendent carboxylic acid by a subscripted 'C', a pendent alkyldiamine by a subscripted 'NN' and a pendent dicarboxylic acid by a subscripted 'CC'. Thus, the nylon nucleic acid was synthesized with only thymidine and modified uridine. To realize base pairing programmed nylon polymer synthesis, heterobase oligonucleotides or polynucleotides must be utilized. However, the presence of heterobases creates the potential for unproductive coupling between pendent carboxylic acids and the amine groups of adenine, cytosine, and guanine. The other concern is the cross-coupling between distant pendent groups, that is, instead of coupling between adjacent groups to form a linear polyamide linkage, the amino groups of $U_{NN}$ or $U_N$ residues could couple with the carboxyl groups of remote $U_{CC}$ or $U_C$ residues and form undesired amide linkage. Taking into consideration that single-stranded DNA (ssDNA) is very flexible and capable of forming loop structures or even turns of 180°, the chance of this side reaction cannot be excluded, especially with increasing numbers of modified residues incorporated into the strand.

Here, the strategy of DNA templated nylon nucleic acid synthesis was used to avoid these undesired cross couplings (FIGS. 2A and 2B). A DNA double helix has much less flexibility than single stranded DNA (Hagerman, 1985). The persistence length of double helical DNA, a measure of its stiffness, is about 50 nm, which corresponds to about 150 base pairs. At lengths well below this size, double-stranded DNA (dsDNA) behaves as a rather rigid polymer, and, therefore, the relatively strict distance between nucleotides will prevent the occurrence of undesired cross coupling. Furthermore, in the DNA double helix, the nucleobases pair with each other and are cloaked inside the helix, so the chance of cross coupling of pendent carboxyl groups with nucleobases should be all but eliminated.

The syntheses of nylon nucleic acid phosphoramidite monomers and oligonucleotides containing nylon nucleic acid precursors were performed as described earlier (Zhu et al., 2003), except that the strands were cleaved from the solid support and deprotected at 50° C., rather than at room temperature. To test the chemical compatibility of templated nylon nucleic acid synthesis, heterodeoxynucleotides (dT, dA, dC and dG) were included. The 18-mer precursor strands were designed to contain a central sequence of eight thymidines that could be substituted systematically with up to eight contiguous pendent uridines (Table 1).

TABLE 1

Oligonucleotides used in this study and MALDI-TOF MS analysis

| ODNs | Sequence[a] | | Calculated | Found |
|---|---|---|---|---|
| 1 | 5'-GCATAGTTTTTTGTCTAC | (SEQ ID NO: 4) | — | — |
| 2 | 5'-GCATATTTTTTTTCTAC | (SEQ ID NO: 5) | — | — |
| 3a | 5'-GCATAGTTUnUcTTGTCTAC | | 5678.9 | 5678.8 |
| 3b | 5'-GCATAGTTUnUcTTGTCTAC | | 5660.9 | 5661.3 |
| 4a | 5'-GCATAGTTUcUnnUcTGTCTAC | | 5840.8 | 5838.9 |
| 4b | 5'-GCATAGTTUcUnnUcTGTCTAC | | 5804.8 | 5803.9 |
| 5a | 5'-GCATAGTTUnUccUnTGTCTAC | | 5840.8 | 5839.5 |
| 5b | 5'-GCATAGTTUnUccUnTGTCTAC | | 5804.8 | 5803.7 |
| 6a | 5'-GCATAGTUcUnnUccUnTGTCTAC | | 6000.4 | 6000.3 |
| 6b | 5'-GCATAGTUcUnnUccUnTGTCTAC | | 5946.4 | 5947.0 |
| 7a | 5'-GCATAGTUcUnnUccUnnUcGTCTAC | | 6161.7 | 6161.9 |
| 7b | 5'-GCATAGTUcUnnUccUnnUcGTCTAC | | 6089.7 | 6090.9 |
| 8a | 5'-GCATAGUcUnnUccUnnUccUnGTCTAC | | 6322.9 | 6323.0 |
| 8b | 5'-GCATAGUcUnnUccUnnUccUnGTCTAC | | 6232.9 | 6233.9 |

TABLE 1-continued

Oligonucleotides used in this study and MALDI-TOF MS analysis

| ODNs | Sequence[a] | Calculated | Found |
|---|---|---|---|
| 9a | 5'-GCATAUcUnnUccUnnUccUnnUccUnTCTAC | 6594.6 | 6594.6 |
| 9b | 5'-GCATAUcUnnUccUnnUccUnnUccUnTCTAC | 6468.6 | 6468.6 |

[a]ODN 1 is an unmodified DNA control for 3a/3b-8a/8b, 2 is an unmodified DNA control for 9a and 9b. ODNs 3a-9a are uncoupled precursor strands with 2, 3, 3, 4, 5, 6 or 8 modified nucleotides incorporated, and 3b-9b contain corresponding nylon nucleic acid sequences.

Figure 3:
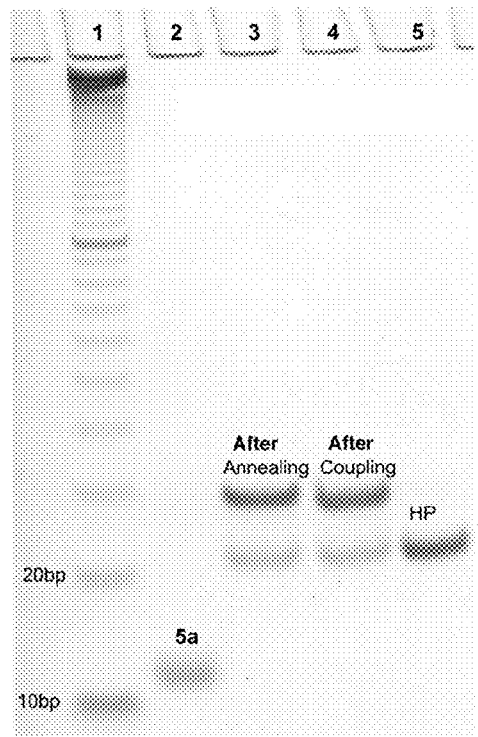

This central sequence was flanked on both sides by heteronucleotide sequences. To facilitate the subsequent purification, a 46-mer complementary hairpin DNA was designed as a template. After routine purification by HPLC or gel electrophoresis, both the precursor strands and the complementary hairpin were desalted by reverse-phase HPLC. This procedure is crucial to eliminate side reactions in the next coupling step. The templated synthesis was begun by annealing the precursor strands with the complementary DNA hairpin to form a duplex. In the presence of the coupling reagent, 4-(4, 6-dimethoxy-1,3,5-triazin-2-yl)-4-methylmorpholinium chloride (DMTMM), 2'-mercaptoalkyl pendent groups were ligated to form a polyamide linkage. Both after annealing and after coupling, an aliquot of solution was removed and subjected to non-denaturing gel electrophoresis, which confirmed that the oligonucleotides were still in the duplex form. In FIG. 3, uncoupled precursor strand 5a and the hairpin are shown in lanes 2 and 5 of the electrophoretogram. A mixture containing a slight excess of hairpin and 5a results in a new band indicating duplex formation shown in lane 3; similar observations can be made for hairpin and nylon nucleic acid 5b in lane 4. The excess of hairpin ensures that amide formation occurs in the context of duplex DNA.

The coupled nylon nucleic acid molecule was separated from the template hairpin by denaturing gel electrophoresis. A series of nylon nucleic acid sequences containing 1 to 7 amide bonds aligned by all four natural heterobase nucleotides was synthesized by this method.

MALDI-TOF MS analysis of nylon nucleic acid. Both the synthetic precursor strands and the nylon nucleic acids were characterized by MALDI-TOF mass spectrometry. As shown in Table 1, observed masses compared well with theory in the MALDI-TOF MS analysis. The coupling yields were estimated conservatively with MALDI-TOF MS by integrating all observed peaks and comparing with the product molecular ion (M+1).

Figure 4A:
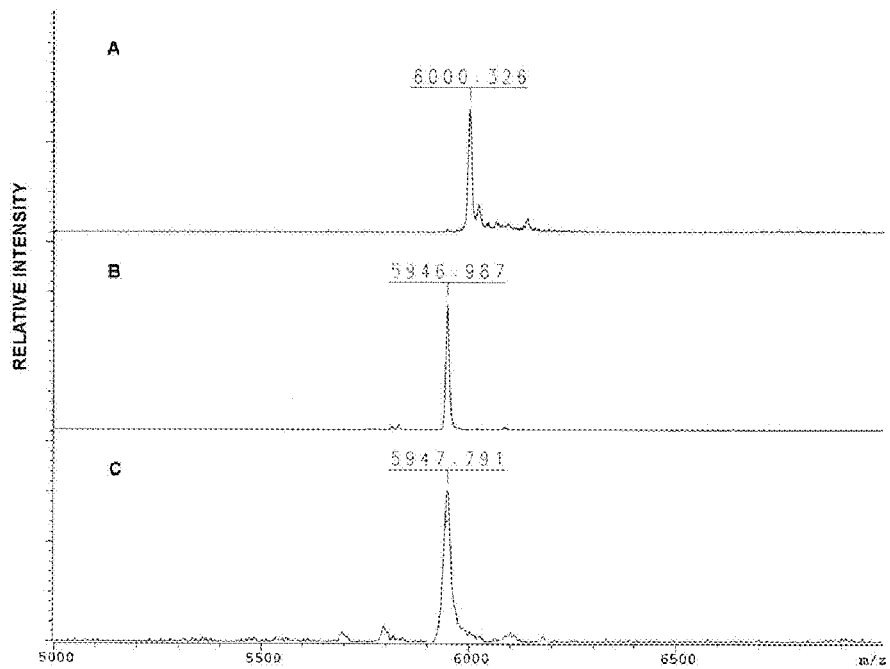
Figure 4B:
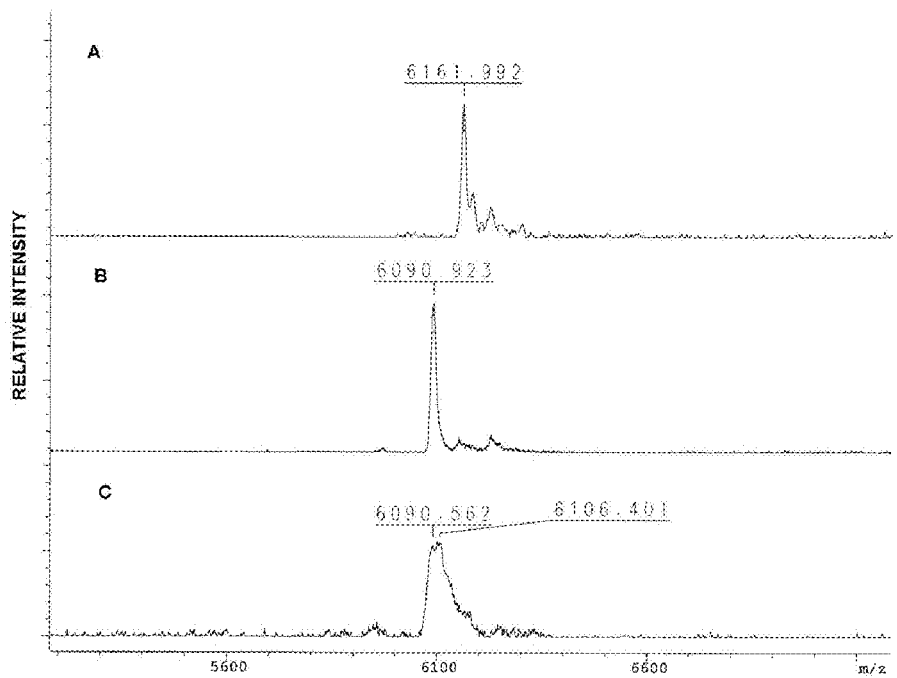
Figure 5A:
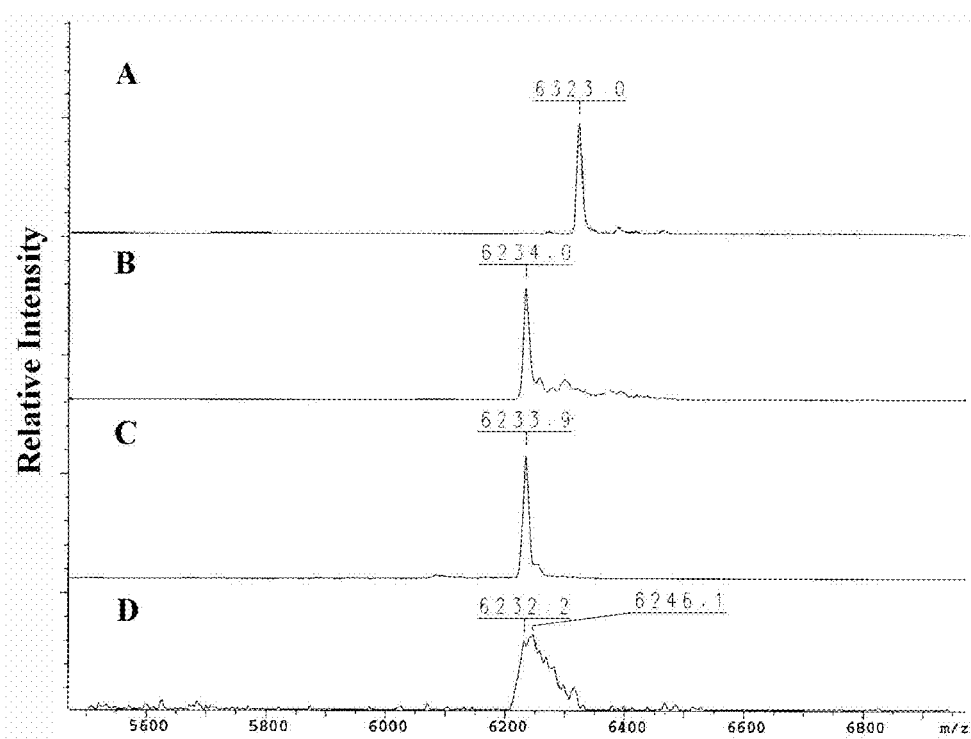
FIG. 5B is a MALDI-TOF mass spectra of (A) the precursor strand 9a and (B) DNA templated synthesis of nylon nucleic acid 9b.
Figure 5B:
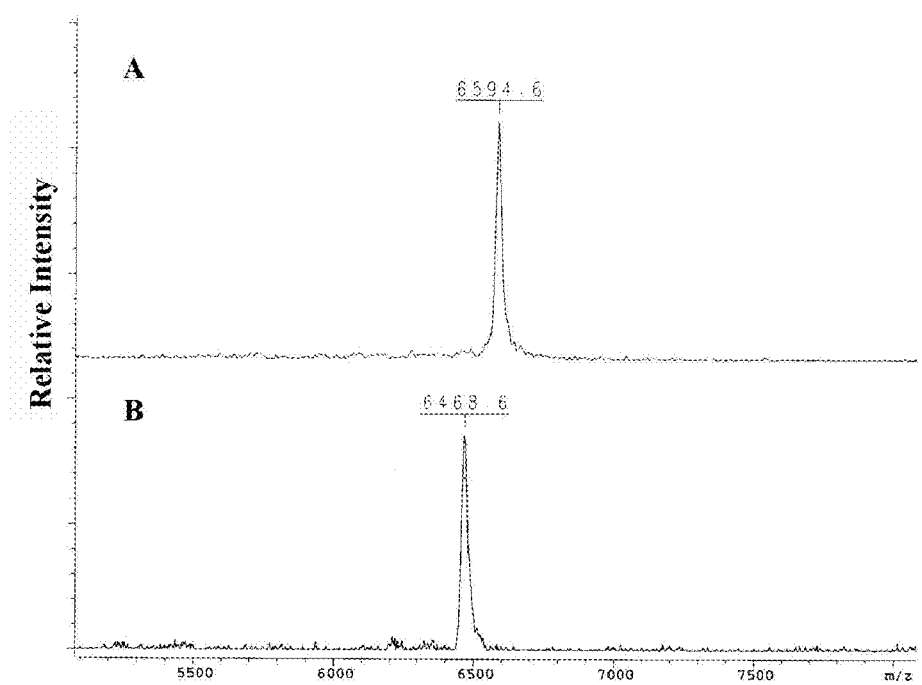

Coupling reactions using only unpaired single strands of 6a, 7a and 8a were performed to compare with temptation by the hairpin. The single-stranded synthesis of 6b gave the anticipated product in 91% estimated yield (FIG. 4A). However, for nylon nucleic acid 7b, though the desired product peak was still observed in the MALDI-TOF mass spectrum, side peaks appeared in high intensity, which led to only 28% yield (73% per amide) for single stranded synthesis (FIG. 4B). The mass pattern became even broader for nylon nucleic acid 8b, where the multiple side peaks form a hump with nearly obscured product mass peak (FIG. 5A) and the yield dropped further to 21% for single-stranded coupling (73% per amide). The poor coupling efficiency of single-stranded synthesis of higher oligomers may originate from the unwanted cross couplings mentioned above, which can form amide bonds either between distant pendent groups or between nucleobases and pendent carboxyl functions. Such reactions may leave adjacent pendent groups unreacted, or may change the geometry of the single strand and keep some pendent groups out of coupling distance.

In contrast to single-stranded synthesis, duplex DNA-templated syntheses of nylon nucleic acids 3b-7b afforded about 96% yield, which corresponds to >95% yield for each coupling step. However, step yields were slightly lower for higher oligomers 8-9, so the protocol was modified to include a second addition of DMTMM after 24 h. This method produced 8b and 9b in 92 and 94% yield, which corresponds to >99% step yields for these reactions. The MALDI-TOF MS results demonstrate that templated nylon nucleic acid synthesis can afford high yield products even with the formation of multiple amide bonds, consistent with the expectation that the DNA temptation positions the pendent groups so that adjacent groups react efficiently.

Controlled exonuclease digestion of nylon nucleic acid. The ODN sequence can be determined by mass spectral analysis of the ODN ladders produced by sequential removal of nucleotides with exonuclease. Individual mononucleotides are identified from the mass differences between adjacent peaks corresponding to product ions from enzymatic cleavage (Pieles et al., 1993).

Figure 6A:
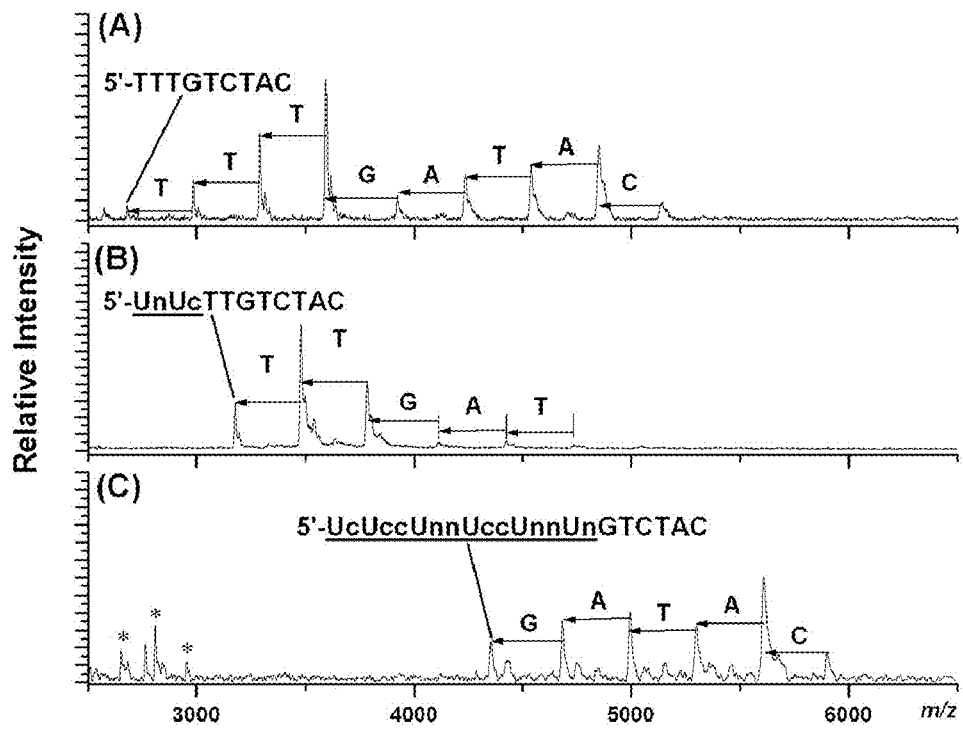
FIG. 6A is MALDI-TOF mass spectra of phosphodiesterase II (CSP) digests of DNA 1 at 0.5 min (A), nylon nucleic acid 3b at 2 min (B) and 8b at 4 min (C). The signals corresponding to doubly charged ions are marked with an asterisk (*)
Figure 6B:
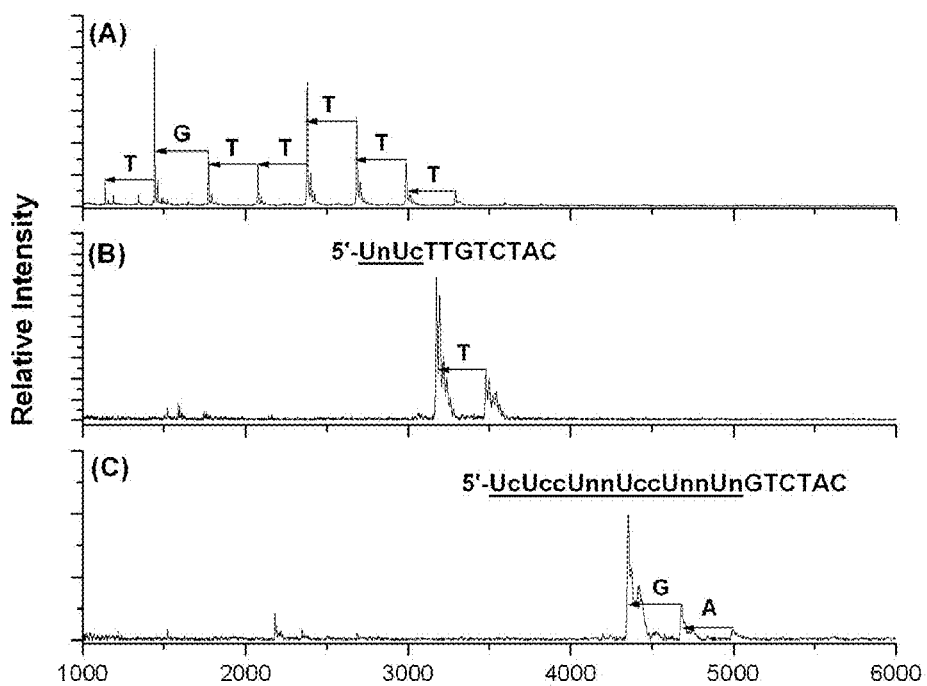
FIG. 6B is MALDI-TOF mass spectra of phosphodiesterase II (CSP) digests of DNA 1 at 2 min (A), nylon nucleic acid 3b at 15 min (B) and 8b at 15 min (C).
Figure 7:
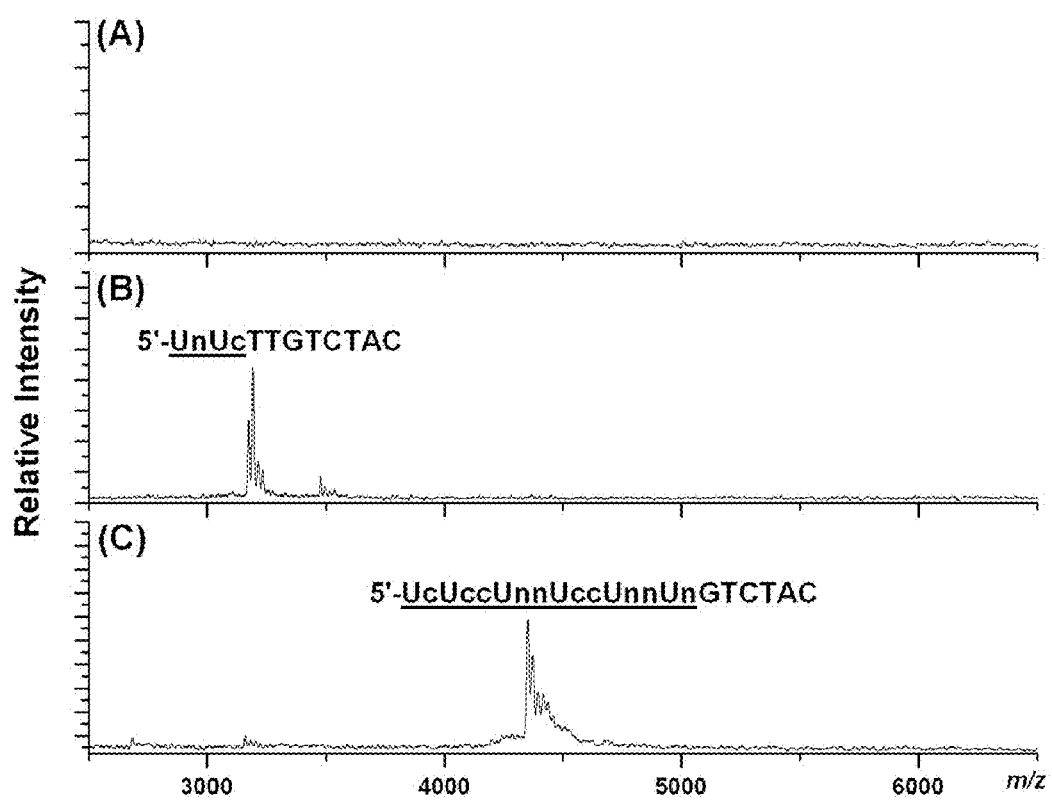
FIG. 7 shows MALDI-TOF mass spectra of phosphodiesterase II (CSP) digests of DNA 1 at 1 h (A), nylon nucleic acid 3b at 4 h (B) and 8b at 4 h (C).

To locate the modified regions of nylon nucleic acid, controlled exonuclease digestion was performed on the template-synthesized nylon nucleic acid 3b and 8b with DNA 1 as a control, and monitored as a function of time. Phosphodiesterase II (calf spleen phosphodiesterase, CSP) served as the exonuclease, cleaving from the 5'-terminus. The MALDI-TOF mass spectra revealed mass ladders for oligonucleotide sequencing from the 5'-end (FIG. 6A). In 2 min, the digestion of 3b reached modified nucleotides UnUc. It took 4 min for the digestion of 8b to move to the modified region. Control DNA 1 showed clear 9-17-mer ladder patterns (the lower mass range was obscured by doubly charged ions) in 0.5 min. With extension of digestion time, 4-9-mer ladders of DNA 1 were observed (FIG. 6B) and in 1 h no DNA fragments longer than trimer were detected (the masses of 1-3-mer fall in the mass range dominated by matrix ions, FIG. 7A). In contrast, digestions of 3b and 8b stopped at modified nucleotides and, even after 4 h, no degradation was detected for either the 5'-UnUcTTGTCTAC fragment from 3b or the 5'-UcUnnUc-cUnnUccUnGTCTAC fragment from 8b (FIG. 7B, 7C). It has been reported that CSP is inhibited by sugar-modified nucleotides (Pieles et al., 1993) and not by base-modified nucleotides, so these CSP digestion results are consistent with the 2'-ribose modification present in nylon nucleic acids. Furthermore, the sequence information about modified nucleotides from the 5'-end within nylon nucleic acids were also verified.

Complete nuclease digestion of nylon nucleic acid. HPLC or LCMS analysis of nucleoside fragments generated from complete nuclease digestion of nucleic acids can provide precise information about base identity and composition. Thus, if nylon nucleic acid could be fully degraded by nuclease, a linear fragment consisting of uridine nucleosides linked only at the 2'-position by a polyamide should result.

Figure 8:
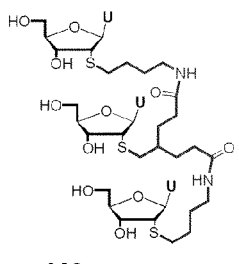
FIG. 8 shows structures of uridine oligoribonucleosides yielded from complete nuclease digestion of nylon nucleic acids.
Figure 8:
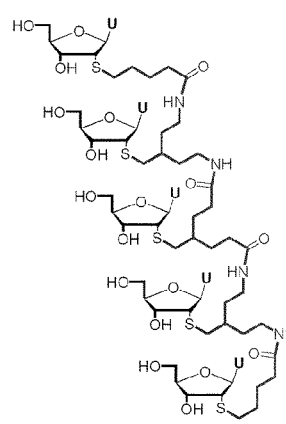
Figure 8:
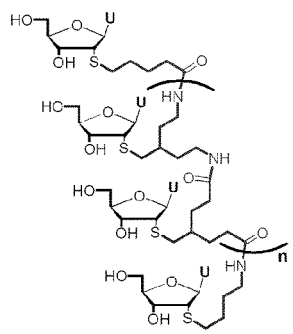
Figure 8:
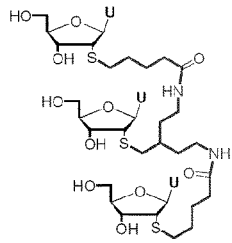
Figure 9:
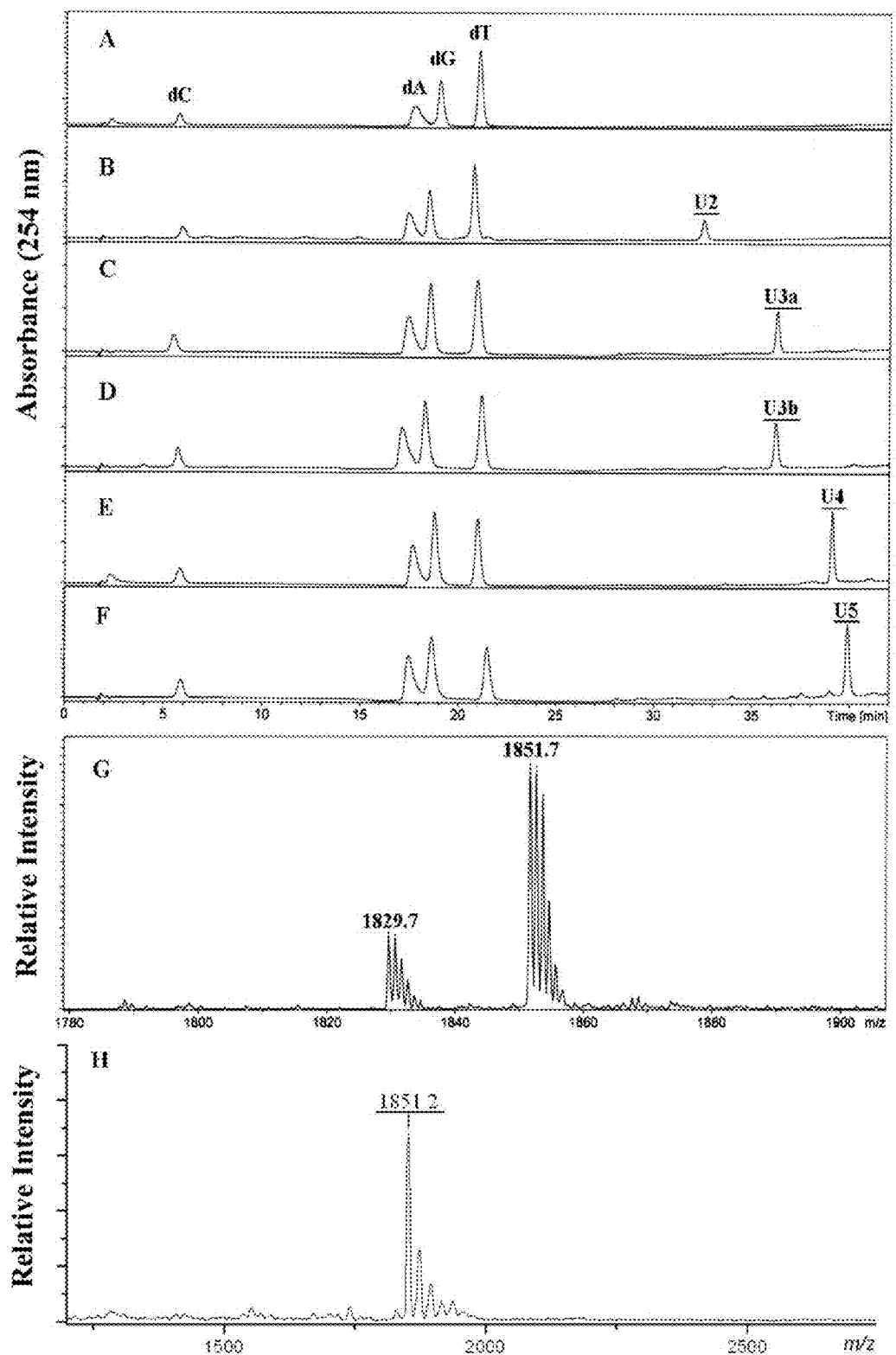
FIGS. 9A-9H show an LCMS analysis of DNA 1 and nylon nucleic acids 3b-7b complete nuclease digestion products using Zorbax C18 column (2.1 mm×150 mm, 5 µm, Agilent Technologies) and MALDI-TOF mass spectrum of U5.
Figure 10:
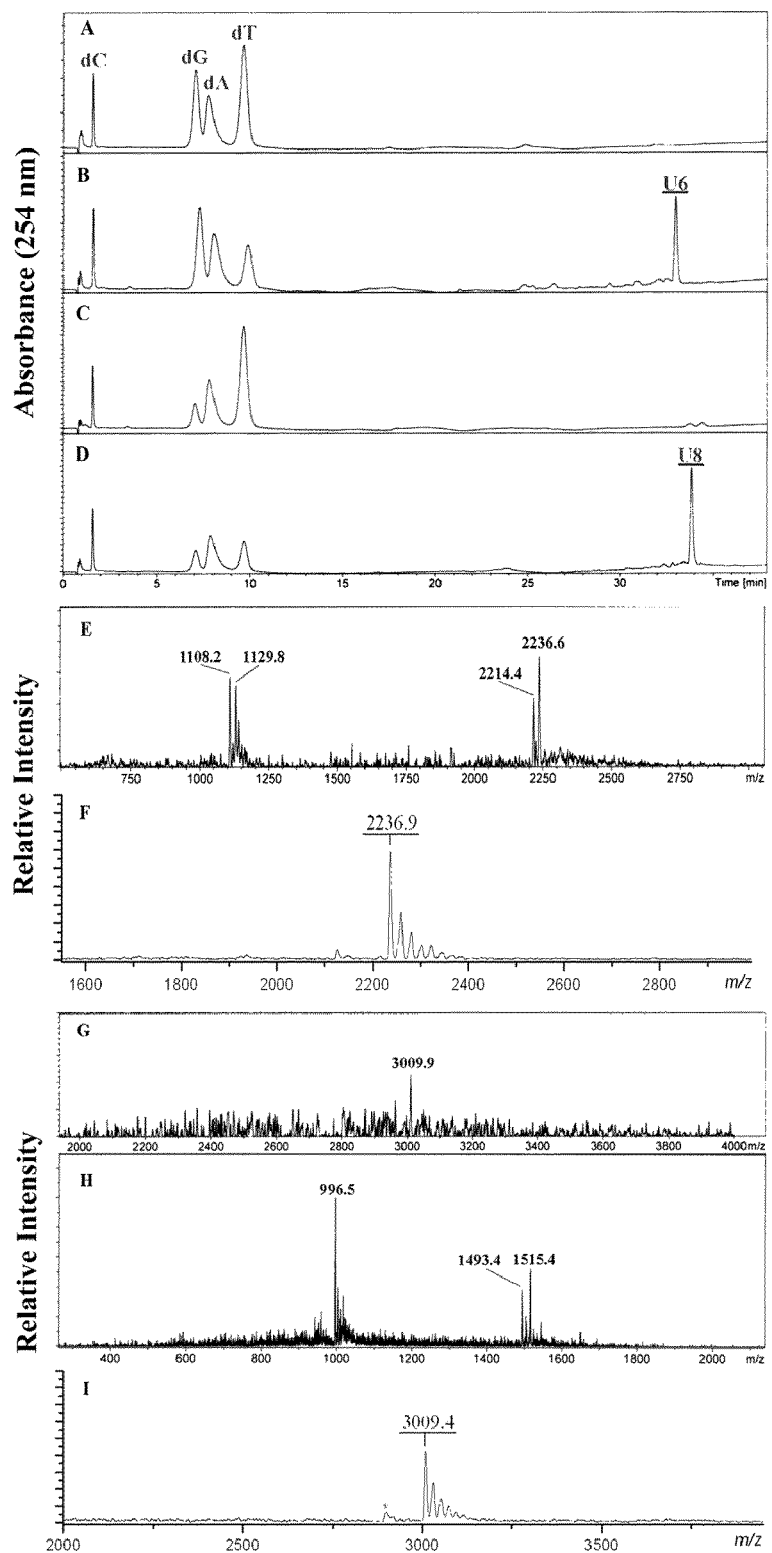
FIGS. 10A-10I show an LCMS analysis of DNA 1, 2 and nylon nucleic acids 8b, 9b complete nuclease digestion products using Zorbax C8 column (2.1 mm×50 mm, 5 µm, Agilent Technologies) and MALDI-TOF mass spectra of U6 and U8.
Figure 11:
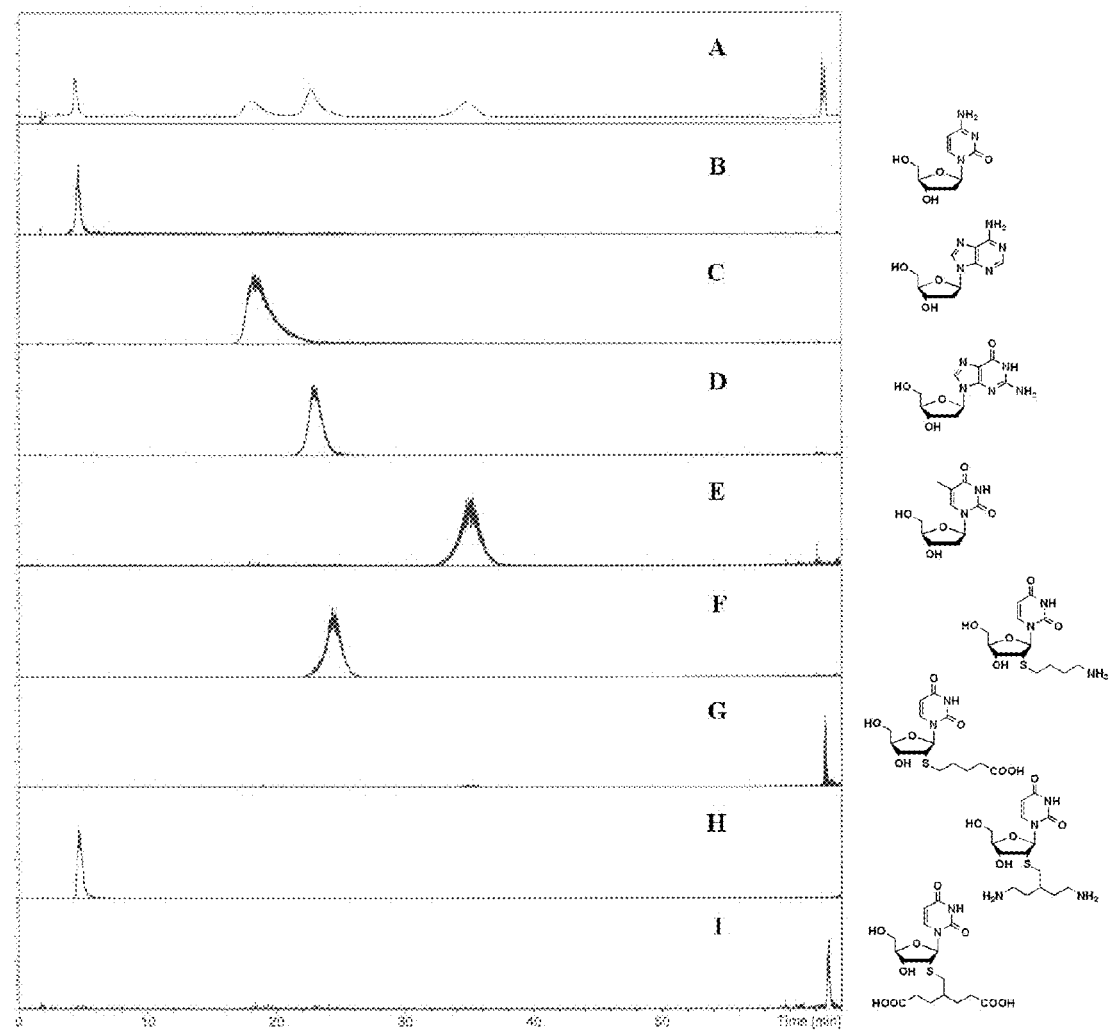
FIGS. 11A-11I show an LCMS analysis of the uncoupled precursor strand 6a complete nuclease digestion products using Zorbax C18 column (2.1 mm×150 mm, 5 µm, Agilent Technologies).
Figure 12:
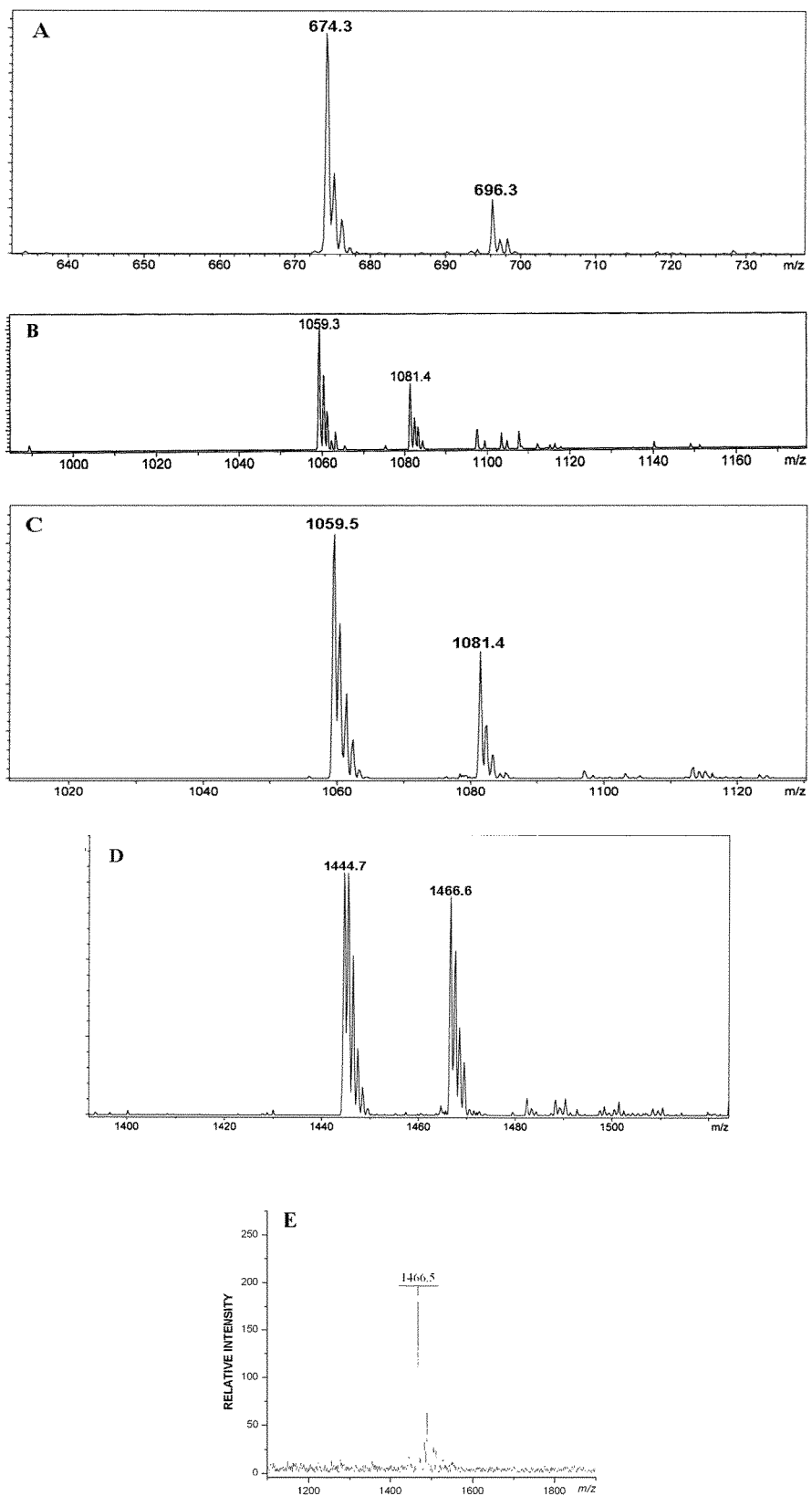
FIGS. 12A-12D are ESI mass spectra (under ultra scan mode) of oligouridine nucleoside fragments from LCMS analysis of nylon nucleic acid complete nuclease digestion.
(FIG. 12E) MALDI-TOF mass spectrum of U4 purified by HPLC, only [M+Na]$^+$ and [M+2Na]$^{2+}$ peaks shown.

Without phosphodiester linkages, these uridine oligomers protrude from the polyamide backbone via the 2'-sulfide tether. Here, U2, U3a, U3b, U4, U5, U6 and U8 are used to designate the uridine oligomers resulting from the digestion of nylon nucleic acid molecules 3b, 4b, 5b, 6b, 7b, 8b and 9b, respectively (FIG. 8). In contrast, any cross-coupled isomers or other byproducts from nylon nucleic acid synthesis would not afford these unique oligomers but would produce other, shorter fragments. The ratio of product nucleosides, both normal nucleosides and amide-linked oligouridine, should agree with the base composition of individual strands, based on analysis of the UV chromatogram.

Phosphodiesterase I (snake venom phosphodiesterase, SVP) and bacterial alkaline phosphatase (BAP) served to catalyze the complete digestion of nylon nucleic acids. Reaction products were analyzed by LCMS. First, a Zorbax C18 analytical column (Agilent Technologies) was used to separate the digestion products. For 3b, 4b, 5b, 6b and 7b, UV chromatograms showed five peaks (FIGS. 9A-9H). In order of elution, these peaks were identified as dC, dA, dG, dT (Eadie et al., 1987; Andrus et al., 2000) and a strongly retained fragment whose mass value and isotopic pattern were consistent with expectations for U2, U3a, U3b, U4 and U5, respectively. The LCMS eluent contains 0.1% formic acid (C18 column) to facilitate the coupled ESI-MS analysis, so the elution order of nucleosides is different from that reported for neutral RP-HPLC analysis on a C18 column (dC, dG, dT, dA). The nucleoside elution order under the slightly acidic conditions is dC, dA, dG and dT on a C18 column, which was confirmed by mass data and also by control experiments with commercial nucleosides and digests of unmodified DNA.

Correlating with the number of uridine residues, the retention time of these oligomers increased in the following order: U2<U3a≈U3b<U4<U5. Though in different sequences, U3a and U3b both have three residues and therefore displayed very similar retention times. A C8 column was required for the analysis of the more hydrophobic U6 and U8 (FIG. 10A-10I). Under the same elution conditions, retention times were shorter and the elution order changed to dC, dG, dA, dT and uridine oligomers. On a C8 column the nucleosides elution order under slightly acidic LCMS conditions is dC, dG, dA and dT, which is different from C18 column separation in the same LCMS conditions (dC, dA, dG and dT) and also the neutral HPLC C18 column separation (dC, dG, dT and dA) (For example, compare FIG. 9A with FIG. 10A, where the same digestion products from DNA 1 were separated on C18 and C8 columns). Commercial nucleosides and digests of normal DNA were used to verify the observation.

The ESI MS of U6 and U8 afforded peaks corresponding to both singly- and doubly-charged molecules by adjusting instrument parameters (FIGS. 10A-10I). The UV chromatogram also showed that U8 had a slightly longer retention time than U6. Integration ratios from all UV chromatograms were measured, and the relative ratios of the five components (dC, dA, dG, dT and oligouridine) were consistent with the base composition of the individual strands (Table 2).

TABLE 2

Relative integrated areas calculated from UV chromatogram of LCMS analysis of DNA and nylon nucleic acids.[a, b, c, d]

| ODNs | Deoxycytidine (dC) | Deoxyadenosine (dA) | Deoxyguanosine (dG) | Thymidine (dT) | Oligonucleosides |
|---|---|---|---|---|---|
| 1  | 1 | 3.27 (3.31) | 3.84 (3.79) | 6.71 (6.67) | — |
| 2  | 1 | 3.35 | 1.30 | 8.20 | — |
| 3b | 1 | 3.35 | 3.81 | 5.32 | 1.36 (U2) |
| 4b | 1 | 3.16 | 3.80 | 4.50 | 1.68 (U3a) |
| 5b | 1 | 3.36 | 3.65 | 4.22 | 1.78 (U3b) |
| 6b | 1 | 3.15 | 3.88 | 3.69 | 2.23 (U4) |
| 7b | 1 | 3.14 | 3.61 | 2.99 | 2.47 (U5) |
| 8b | 1 | 3.31 | 3.83 | 2.36 | 2.56 (U6) |
| 9b | 1 | 3.33 | 1.24 | 2.35 | 2.83 (U8) |

[a] Relative integration areas for 1, 3b-7b are obtained from UV chromatogram on C18 column, Relative integration areas for 1 (data in parenthesis), 2, 8b and 9b are obtained from UV chromatogram on C18 column.
[b] The relative integrated areas refer to the ratio of the integrated areas of individual UV peaks to the integrated area of deoxycytidine (dC) in the same UV chromatogram.
[c] Measured at pH 4.0, 25° C., 254 nm.
[d] The released dC, dA and dG residues showed similar ratios in UV chromatograms of 1, 3b-8b. However, the relative ratios of deoxythymidine (dC of each chromatogram as standard) from 1 to 8b were: 6.67 (1):5.32 (3b):4.50 (4b):4.22 (5b):3.69 (6b):2.99 (7b):2.36 (8b). Taking into account the same number of dT residues in sequences 4b and 5b, the decrease of dT ratios was consistent with the number of dT residues in each strand. In contrast, the relative ratios of uridine oligomers were: 1.36 (U2):1.68 (U3a):1.78 (U3b):2.23 (U4):2.47 (U5):2.56 (U6):2.83 (U8). Again, except for U3a and U3b with same number of uridines, there was a clear trend that longer oligomers have a higher ratio. Comparing UV chromatogram of digests of nylon nucleic acid 9b and its control 2, the relative ratio of dT was 2.35(9b):8.20(2) close to 3:11 real ratio. Finally, 8b and 9b had similar ratios of dC, dA and dT, but dG was in 3.83(8b):1.24(9b), which was compares favorably with the actual 3:1 dG ratio.

Shorter uridine oligomers or modified uridines linked with other nucleosides were not detected. These results indicate that templated synthesis produces nylon nucleic acid in high yield with coupling only between pendent groups attached to adjacent nucleotides.

As a control, the precursor strand 6a was also subjected to nuclease full digestion and LCMS analysis, affording all eight different nucleosides (dC, dA, dG, dT, Un, Unn, Uc and Ucc; FIGS. 11A-11I). Thus, complete nuclease digestion, coupled with LCMS analysis, provided both identification and quantification of nucleosides.

Hybridization studies of U8 to native DNA. The structure of the nylon oligomers with pendent uridine nucleosides obtained from complete digestion is similar to peptide ribose nucleic acid (PRNA) reported by Wada (Wada et al., 2000; Inoue, 2004). After removal of the phosphate groups, the remaining compounds are oligoamides with DNA nucleosides (uridine in this case) protruding from the polymer backbone. The binding affinity of these neutral oligomers to native DNA was examined.

The isolated U4, U5, U6 and U8 nylon ribonucleosides were characterized by MALDI-TOF MS and, because of their neutral structure, α-cyano-4-hydroxycinnamic acid (CHCA) was used as the matrix. The mass signals corresponding to [M+Na+] adducts were detected, which was in accord with LCMS measurements (FIG. 9H, FIG. 10F, FIG. 10I and FIG. 12E). Therefore, these data have provided additional support for the assigned structures of nylon nucleic acids afforded by template synthesis.

Because the study of the stable duplex with oligodeoxyadenosine (dA) requires at least a heptamer (Brahms et al., 1966; Giham, 1966), the synthesis and purification of U8 was scaled up. The hybridization behavior of the polyamide-linked U8 with a phosphate-linked deoxyadenosine octamer (dA8) was assessed by thermal denaturing experiments. In light of reports (Ross et al., 2003; Howard, 2005) that oligonucleotides containing dT formed more stable duplexes than analogous strands containing dU, the phosphate-linked deoxyuridine octamer (dU8) was synthesized and served as a control for U8.

Figure 13A:
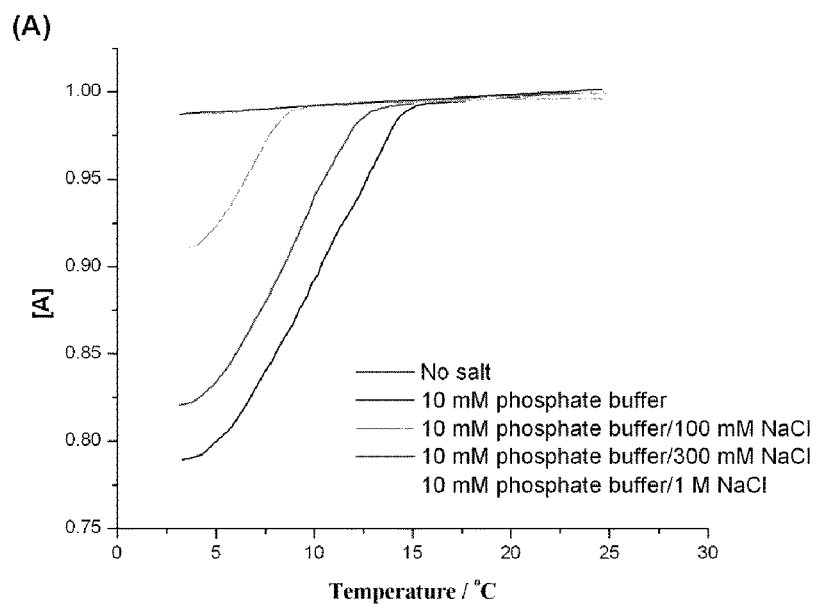
FIGS. 13A and 13B are graphs showing the melting curves under the indicated salt conditions for (FIG. 13A) U8 dA$_8$, and (FIG. 13B) dU$_8$:dA$_8$. [A]=A$_T$/A$_{max}$. (A$_{max}$ are the absorbance at 25° C. for (FIG. 13A) and the absorbance at 40° C. for (FIG. 13B)). UV absorption was monitored at 260 nm with 1 mm pathlength cell. Duplex concentration: 37 µM.
Figure 13B:
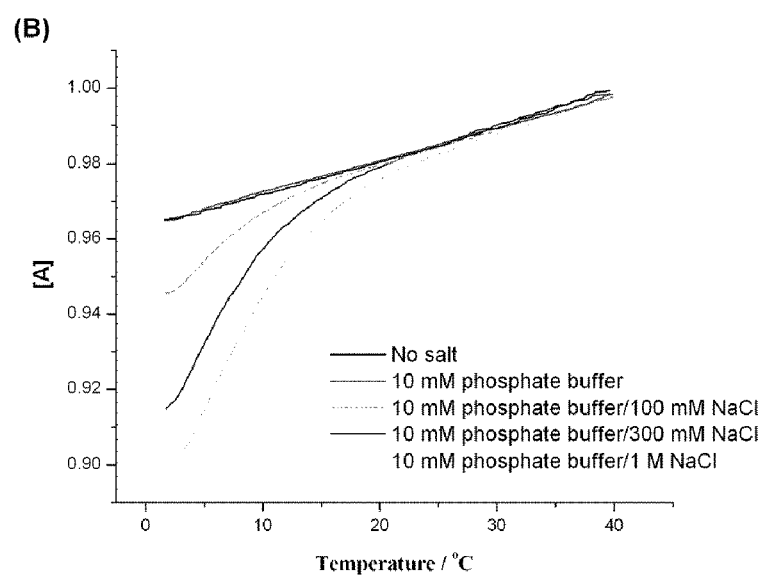
Figure 14:
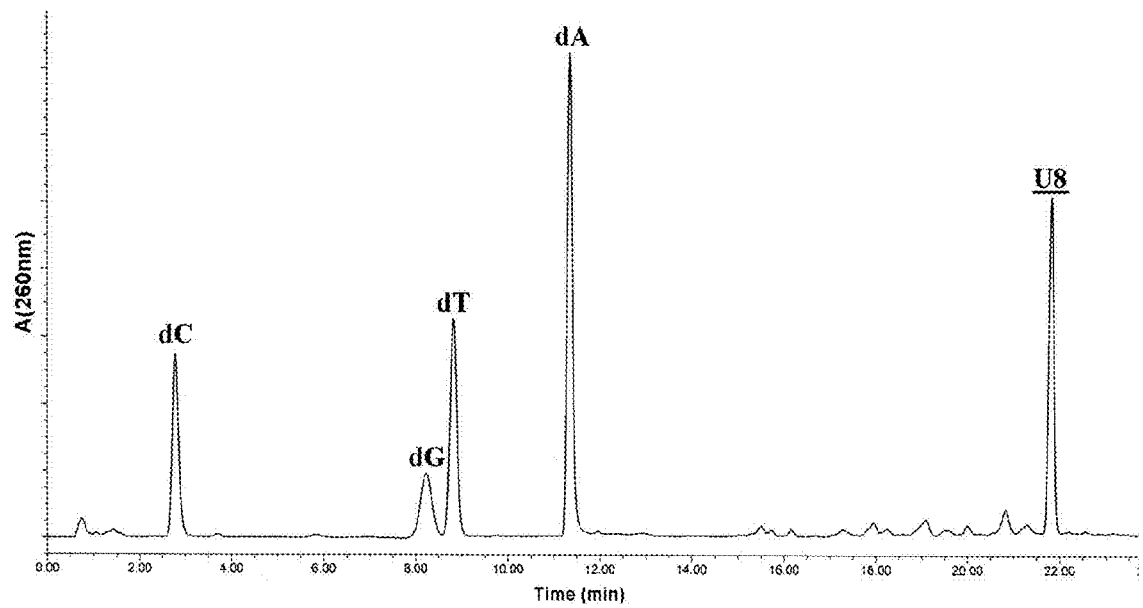
FIG. 14 is a UV chromatogram of HPLC separation of nylon nucleic acid 9b complete nuclease digestion products using Zorbax C8 column (4.6 mm×50 mm, 5 µm, Agilent Technologies).

The stability of the U8: dA8 duplex showed a marked inverse dependence on salt concentration (FIG. 13A). In the absence of salt, a cooperative melting curve was observed with a melting temperature ($T_m$) at about 10° C. Addition of salt to the sample destabilized the duplex; Tm decreased to 8.7° C. in 10 mM sodium phosphate buffer and further dropped to 6.5° C. in 100 mM NaCl. No melting transition was detected above 300 mM NaCl. In contrast, the binding affinity of dU8:dA8 exhibited the usual nucleic acid trend, showing a direct dependence on salt concentration (FIG. 13B). Under salt-free and low salt (10 mM phosphate) conditions, no UV transition normally associated with association/dissociation of duplex was observed. With the increase of salt concentration from 100 mM NaCl to 1 M NaCl, a clear enhancement of the UV transition was shown. For unmodified DNA duplexes, it is known that high sodium cation concentration can counteract the negatively charged phosphate backbone and increase the helix stability (Bloomfield et al., 2000). For neutral DNA analogs, such as PNA (Sen et al., 2006) and amide-linked polythymidine (Lund et al., 2006; Seeman, 2005(c); Seeman et al., 2005(d); Niemeyer et al., 2006), it has been reported that increasing salt concentration impairs binding to DNA; this finding was rationalized as differential stabilization of the phosphate-containing single strand. Nevertheless, the present nylon oligoribonucleoside hybridized with its DNA complement and formed a stable duplex in water and low salt buffer. In addition, no solubility problem was found for this neutral DNA analog, possibly owing to the presence of the hydrophilic ribose moieties. Moreover, since it was generated by complete nuclease digestion of nylon nucleic acids, the nuclease resistance of this DNA analogue is certain. This nylon-linked oligonucleoside is the first DNA analog produced from complete nuclease digestion of another DNA analogue. It may have application in some special environments unsuitable for unmodified DNA or other DNA analogs, such as binding DNA in low dielectric media.

Conclusions

A series of hybrid nylon nucleic acid strands containing heterobase nucleotides was synthesized by DNA temptation. To evaluate the efficiency of synthesis and clarify the chemical structure of nylon nucleic acids, a variety of analytical techniques were employed. First, MALDI-TOF MS analysis demonstrated that nylon nucleic acid molecules with up to 7 amide linkages were synthesized in high yield; the efficiency of templated coupling reactions was markedly greater than in single stranded coupling. Second, modified nucleotide regions were identified by controlled exonuclease digestion, coupled with MALDI-TOF analysis. Finally, a combination of complete nuclease digestion with LCMS analysis or HPLC-MALDI-TOF analysis established that the nylon nucleic acids were coupled only to amines/carboxylates from neighboring nucleotides and verified that the 2'-amide linker formation was in a linear arrangement and was compatible with the presence of heterobase nucleotides. The success of DNA templated synthesis of nylon nucleic acid provides a practical strategy to assemble organic polymers under the direction of DNA, which is another step toward our long-term goal of using the control afforded by nucleic acids (Zhu et al., 2003; Lund et al., 2006; Seeman, 2005(c); Seeman et al., 2005(d); Niemeyer et al., 2006) to direct the topology of polymers with industrial importance. Furthermore, the complete nuclease digestion of nylon nucleic acid produced a new kind of DNA analogue, a nylon-like polyamide with pendant nucleosides attached via the 2' position of ribose. Thermal denaturing studies revealed that this nylon oligoribonucleoside formed stable duplexes with complementary DNA under conditions that ranged from salt-free to medium salt solutions.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

An et al., 1996, 52, 5179; Bergamin et al., *A. Chem. Commun.*, 2001, 17.

Andrews et al., *J. Chromatogr. A*, 1999, 856:515; Koc et al., *J. Chromatogr. B*, 2002, 778:323

Andrews, C. L.; Vouros, P.; Harsch, A. *J. Chromatogr. A*, 1999, 856, 515.

Andrus, A.; Kuimelis, R. G. *Current Protocols in Nucleic Acid Chemistry*, 2000, 10.6.1-10.6.6.

Asara, J. M.; Hess, J. S.; Lozada, E.; Dunbar, K. R.; Allison, J. *J. Am. Chem. Soc.*, 2000, 122, 8.

Banoub et al., *Chem. Rev.*, 2005, 105:1896.

Banoub, J. H.; Newton, R. P.; Esmans, E.; Ewing, D. F.; Mackenzie, G. *Chem. Rev.*, 2005, 105, 1896.

Barry et al., *J. Am. Chem. Soc.*, 2003, 125:9629.

Bartolini, W. P.; Bentzley, C. M.; Johnson, M. V.; Larsen, B. S. *J. Am. Soc. Mass Spectrom.*, 1999, 10, 521.

Bath, J.; Turberfield, A. *J. Nat. Nanotechnol.* 2007, 2, 275.

Bloomfield, V. A.; Crothers, D. M.; Tinoco, I. JR. Nucleic Acids Structures, Properties, and Functions, University Science Book: Sausalito, Calif., 2000; pp 475-534.

Box, H. C.; Patrayc, H. B.; Dawidzik, J. B.; Iijima, H.; Freund, H. G.; Higbee, A. J.; Budzinski, E. *Radiat. Res.*, 2002, 158, 538.

Brahms, J.; Michelson, A. M.; Van Holde, K. E. *J. Mol. Biol.*, 1966, 15, 467.

Braun et al., *Nature*, 1998, 391:775; Richter et al., *Appl. Phys. Lett.*, 2001, 78:536.

Briones et al., *Current Nanoscience*, 2006, 2:257.

Burley, G. A.; Gierlich, J.; Mofid, M. R.; Nir, H.; Tal, S.; Eichen, Y.; Carell, T. *J. Am. Chem. Soc.* 2006, 128, 1398-1399.

Chou, C.; Limbach, P. A. *Current Protocols in Nucleic Acid Chemistry*, 2000, 10.1.1-10.1.25.

Datta, B.; Schuster, G. B. *J. Am. Chem. Soc.* 2008, 130, 2965.

Datta, B.; Schuster, G. B.; McCook, A.; Harvey, S. C.; Zakrzewska, K. *J. Am. Chem. Soc.* 2006, 128, 14428-14429.

Eadie et al., *Anal. Biochem.*, 1987, 165:442.

Eadie, J. S.; McBride, L. J.; Efcavitch, J. W.; Hoff, L. B.; Cathcart, R. *Anal. Biochem.*, 1987, 165, 442.

Feldkamp, U.; Niemeyer, C. M. *Angew. Chem. Int. Ed.*, 2006, 45, 1856.

Felsenfeld et al., *J. Am. Chem. Soc.*, 1957, 79:2023.

Freier, S. M. and Altmann, K., The ups and downs of nucleic acid duplex stability: structure-stability studies on chemically-modified DNA:RNA duplexes, *Nucleic Acids Research*, 25(22) 4429-4443 (1997)

Fritz et al., *Science*, 2000, 288:316.

Fritz et al., *Trends Biochem. Sci.*, 2005 30(3) 119.

Hagerman, *Biopolymers*, 1985, 24:1881.

Hagerman, P. J. *Biopolymers*, 1988, 24, 1881.

Harris et al., PNA encoding (PNA=peptide nucleic acid): From solution-based libraries to organized microarrays, *Chem. Eur. J.*, 11:6792-6801 (2005)

He et al., *Chem. Commun.*, 2004, 348

Howard, F. B. Biopolymers, 2005, 78, 221.

Katz Willner, I. *Angew. Chem. Int. Ed.*, 2004, 43:6042.

Katz et al., *ChemPhysChem*, 2004, 5:1084.

Kleiner, R. E.; Brudno, Y.; Birnbaum, M. E.; Liu, D. R. *J. Am. Chem. Soc.* 2008, 130, 4646.

Koc, H.; Swenberg, J. A. *J. Chromatogr. B*, 2002, 778, 323.

Kowalak et al., *J. Biol. Chem.*, 2000, 275:24484

Leitzel, J. C.; Lynn, D. G. *Chem. Rec.*, 2000, 53.

Li et al., *J. Am. Chem. Soc.*, 2005, 127:14.

Li et al., *Nano. Lett.*, 2003, 3:597

Limbach, P. A., *Mass Spectrom. Rev.*, 1996, 15, 297.

Lund et al., *Current Nanoscience*, 2006, 2(2):113.

Lund, K.; Williams, B.; Ke, Y.; Liu, Y.; Yan, H. *Current Nanoscience*, 2006, 2(2), 113.

McCloskey, J. A.; Graham, D. E.; Zhou, S. L.; Crain, P. F.; Ibba, M.; Konisky, J.; Soll, D.; Olsen, G. *J. Nucleic Acid Res.*, 2001, 29, 4699.

McCloskey et al., *Nucleic Acid Res.*, 2001, 29:4699.

Mergny, J.; Lacroix, L. *Oligonucleotides*, 2003, 13, 515.

Merkoci et al. *Trends in Analytical Chemistry*, 2005, 24:341.

Monson et al., *Nano. Lett.*, 2003, 3:359. Keren et al., *Science*, 2003, 302:1380.

Naylor, R.; Giham, P. T. *Biochemistry*, 1966, 2722.

Nielsen, The many faces of PNA, *Letters in Peptide Science*, 10:135-147 (2003)

Pieles, U.; Zucher, W.; Schar, M.; Moser, H. E. *Nucleic Acid Res.*, 1993, 21, 3191.

Roberts et al., *J. Chem. Res. Toxicol.*, 2006, 19:300

Ross, P. D.; Howard, F. B. *Biopolymers.* 2003, 68, 210

Rothemund et al., *Nature*, 2006, 440:297

Sato et al., Synthesis and conformation control of peptide ribonucleic acid (PRNA) containing 5'-Amino-5'-deoxyribopyrimidine and 5'-amino-5'-deoxyribopurine-nucleosides, *Journal of Bioactive and Compatible Polymers*, 19:65-79 (2004)

Sato, K.; Hosokawa, K.; and Maeda, M. *Anal. Sci.*, 2007, 23, 17.

Schmitz, Anal. *Bioanal. Chem.*, 2006, 384:34.

Seeman, N. C. *Methods in Molecular Biology*, 2005(a), 303, 143.

Seeman, N. C.; Lukeman, P. S. *Rep. Prog. Phys.*, 2005(b), 68(1),

Sen, A.; Nielsen, P. E. *Biophys. J.*, 2006, 90, 1329.

Singh, R.; Farmer, P. B. *Carcinogenesis*, 2006, 27, 2, 178.

Smirnov, I. P.; Roskey, M. T.; Juhasz, P.; Takach, E. J.; Martin, S. A. Haff, L. A. 1996, *Anal. Biochem.*, 238, 19.

Staii et al., A. *Nano. Lett.*, 2005, 5:1774.

Tretyakova, N.; Matter, B.; Ogdie, A.; Wishnok, J. S.; Tanenbaum, S. R. *Chem. Res. Toxicol.*, 2001, 14, 1058.

Wada et al., Peptide ribonucleic acids (PRNA). 2. A novel strategy for active control of DNA recognition through borate ester formation, *J. Am. Chem. Soc.*, 2000, 122:6900-6910.

Wada, T.; Minamimoto, N.; Inaki, Y.; Inoue, Y. *J. Am. Chem. Soc.*, 2000, 122, 6900.

Wada, T.; Sato, H.; Inoue, Y. *Biopolymers*, 2004, 76, 15.

Xin et al., *Nanotechnology*, 2005, 16:2238.

Zheng et al. C. *Nano. lett.*, 2006, 6:2864.

Zhu et al., *Nucleotides, Nucleosides Nucleic Acids*, 2002, 21:723.

Zhu, L.; Lukeman, P. S.; Canary, J. W.; Seeman, N. C. *J. Am. Chem. Soc.*, 2003, 125, 10178.

Zuccheri et al., 2005, 1:590.

What is claimed is:

1. A nylon polyribonucleoside molecule, comprising the formula (III)

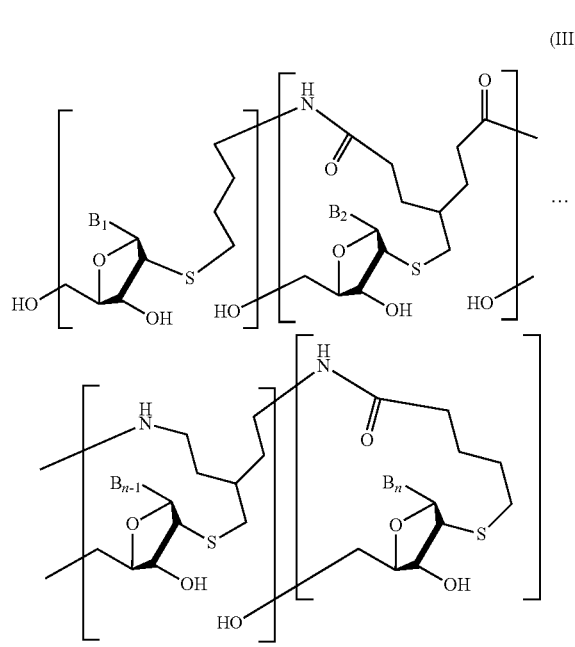

(III)

wherein $B_1$ to $B_n$ independently is a base selected from the group consisting of uracil, thymine, adenine, guanine, cytosine, and modified pyrimidine and purine bases.

2. The nylon polyribonucleoside molecule of claim 1, wherein n is in a range of 5 to 50 for $B_n$.

3. The nylon polyribonucleoside molecule of claim 1, wherein n is in a range of 8 to 40 for $B_n$.

4. The nylon polyribonucleoside molecule of claim 1, wherein n is in a range of 10 to 30 for $B_n$.

5. A method for preparing the nylon polyribonucleoside molecule of claim 1, comprising enzymatically digesting a nucleic acid molecule of formula (IV) with a phosphodiesterase enzyme and a phosphatase enzyme to prepare the nylon polyribonucleoside molecule of formula (III)

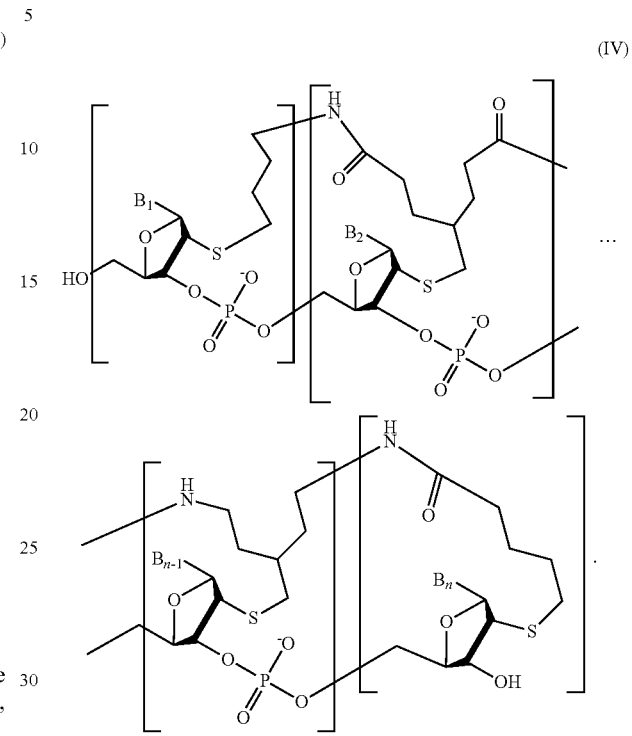

(IV)

6. The method of claim 5, wherein the phosphodiesterase enzyme is snake venom phosphodiesterase (SVP) and the phosphatase enzyme is bacterial alkaline phosphatase (BAP).

* * * * *